(12) United States Patent
Steinmann et al.

(10) Patent No.: US 11,304,811 B2
(45) Date of Patent: *Apr. 19, 2022

(54) SURGICAL IMPLANT DEVICES INCORPORATING POROUS SURFACES AND ASSOCIATED METHOD OF MANUFACTURE

(71) Applicant: Kyocera Medical Technologies, Inc., Redlands, CA (US)

(72) Inventors: John C. Steinmann, Redlands, CA (US); Scott Rucker, Austin, TX (US); Tim Rasmussen, Redlands, CA (US); John P. Steinmann, Redlands, CA (US); Trace Cawley, Boca Raton, FL (US); Thomas Ross, Austin, TX (US); Ernesto Rios, Austin, TX (US); Andrew Olcese, Austin, TX (US)

(73) Assignee: Kyocera Medical Technologies, Inc., Redlands, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 16/788,353

(22) Filed: Feb. 12, 2020

(65) Prior Publication Data

US 2020/0179123 A1 Jun. 11, 2020

Related U.S. Application Data

(63) Continuation-in-part of application No. 14/339,508, filed on Jul. 24, 2014, now Pat. No. 10,765,530, (Continued)

(51) Int. Cl.
*A61F 2/30* (2006.01)
*A61F 2/34* (2006.01)

(52) U.S. Cl.
CPC .......... *A61F 2/30771* (2013.01); *A61F 2/34* (2013.01); *A61F 2002/3093* (2013.01);
(Continued)

(58) Field of Classification Search
CPC .. A61F 2002/30784; A61F 2002/30841; A61F 2002/3092; A61F 2002/3093;
(Continued)

(56) References Cited

U.S. PATENT DOCUMENTS 7,272,855 B1 9/2007 Yemeni et al.
2007/0225785 A1 9/2007 Park et al.
(Continued)

*Primary Examiner* — Samuel S Hanna
(74) *Attorney, Agent, or Firm* — Clements Bernard Walker; Christopher L. Bernard

(57) ABSTRACT

A surgical implant device, including: an implant body; a porous layer disposed adjacent to the implant body, wherein the porous layer includes a lattice of intersecting struts; and a plurality of needle structures protruding from the porous layer opposite the implant body, wherein at least some of the plurality of needle structures traverse the porous layer and are anchored to the implant body. The plurality of needle structures that traverse the porous layer and are anchored to the implant body are coupled to one or more intersecting struts of the lattice. Optionally, some of the plurality of needle structures are spaced apart from the implant body and are anchored only to the porous layer. Preferably, one or more of the implant body, the porous layer, and the plurality of needle structures are formed by an additive manufacturing technique.

9 Claims, 22 Drawing Sheets

Related U.S. Application Data which is a continuation-in-part of application No. 13/530,048, filed on Jun. 21, 2012, now abandoned.

(60) Provisional application No. 61/916,469, filed on Dec. 16, 2013, provisional application No. 61/885,778, filed on Oct. 2, 2013, provisional application No. 61/857,824, filed on Jul. 24, 2013, provisional application No. 61/595,249, filed on Feb. 6, 2012, provisional application No. 61/587,336, filed on Jan. 17, 2012.

(52) U.S. Cl.
CPC ............ *A61F 2002/30784* (2013.01); *A61F 2002/30841* (2013.01); *A61F 2002/30985* (2013.01); *A61F 2310/00023* (2013.01)

(58) Field of Classification Search
CPC ........ A61F 2002/30985; A61F 2/30771; A61F 2/30907; A61F 2/3094
See application file for complete search history.

(56) References Cited

U.S. PATENT DOCUMENTS

| | | |
|---|---|---|
| 2009/0326671 A1 | 12/2009 | Schofield |
| 2010/0298950 A1* | 11/2010 | McDonnell ......... A61F 2/30771 623/23.53 |
| 2013/0056912 A1 | 3/2013 | O'Neill et al. |

* cited by examiner

SURGICAL IMPLANT DEVICES INCORPORATING POROUS SURFACES AND ASSOCIATED METHOD OF MANUFACTURE

CROSS-REFERENCE TO RELATED APPLICATIONS

The present patent application/patent is a continuation-in-part (CIP) of co-pending U.S. patent application Ser. No. 14/339,508, filed on Jul. 24, 2014, the contents of which are incorporated in full by reference herein. U.S. patent application Ser. No. 14/339,508 claims the benefit of priority of: (1) U.S. Provisional Patent Application No. 61/857,824, filed on Jul. 24, 2013, (2) U.S. Provisional Patent Application No. 61/885,778, filed on Oct. 2, 2013, and (3) U.S. Provisional Patent Application No. 61/916,469, filed on Dec. 16, 2013, the contents of all of which are also incorporated in full by reference herein. U.S. patent application Ser. No. 14/339,508 is also a continuation-in-part (CIP) of U.S. patent application Ser. No. 13/530,048, filed on Jun. 21, 2012, which claims the benefit of priority of: (1) U.S. Provisional Patent Application No. 61/587,336, filed on Jan. 17, 2012, and (2) U.S. Provisional Patent Application No. 61/595,249, filed on Feb. 6, 2012, the contents of all of which are further incorporated in full by reference herein.

FIELD OF THE INVENTION

The present invention relates generally to novel surgical implant devices incorporating porous surfaces. More specifically, the present invention relates to novel surgical implant devices incorporating porous surfaces for enhancing bony fixation and purchase when implanted. These porous surfaces are formed via novel additive manufacturing techniques and, optionally, novel post-processing manufacturing techniques. They include novel lattice structures and needle-like protrusions.

BACKGROUND OF THE INVENTION

When various surgical implant devices, all well known to those of ordinary skill in the art, are placed adjacent to or between bony surfaces, it is desirable that adequate friction is present to hold them in place and that surfaces are available for bony fixation and purchase over time. Accordingly, these surgical implant devices often incorporate mechanically-manufactured friction surfaces or utilize friction coatings or bondings for such purposes. However, these mechanically-manufactured friction surfaces, typically consisting of teeth, grooves, striations, or the like that impart a degree of surface porosity, are often not adequate and do little to promote bony purchase. Similarly, these friction coatings or bondings may delaminate and fail.

Thus, what are still needed in the art are improved surgical implant devices that incorporate essentially-integral friction surfaces that are strong and durable, and that provide adequate surface area for bony fixation and purchase, while still being economical to manufacture. Improved additive and post-processing manufacturing techniques now make this possible.

BRIEF SUMMARY OF THE INVENTION

In one exemplary embodiment, the present invention provides a surgical implant device, including: a body portion; and one or more surfaces including a plurality of protruding structures; wherein the body portion and the one or more surfaces including the plurality of protruding structures are integrally formed. The one or more surfaces including the plurality of protruding structures are formed by an additive manufacturing process. The plurality of protruding structures include a plurality of needles. Optionally, the plurality of protruding structures include a plurality of needles that are disposed substantially perpendicular to the body portion. Alternatively, the plurality of protruding structures include a plurality of needles that are disposed at an angle to the body portion. Preferably, the plurality of protruding structures include a plurality of needles that include titanium. The body portion defines a hollow interior cavity. Optionally, the body portion defines one or more ports that are configured to receive a bone screw. The body portion defines one or more ports that are configured to allow bony ingrowth. The surgical implant device includes one of an anterior lumbar interbody fusion cage, a posterior lumbar interbody fusion cage, a transforaminal lumbar interbody fusion cage, an oblique lumbar interbody fusion cage, a cervical cage, and a bone screw.

In another exemplary embodiment, the present invention provides a method for manufacturing a surgical implant device, including: providing a body portion; and forming one or more surfaces including a plurality of protruding structures on an exterior portion of the body portion; wherein the body portion and the one or more surfaces including the plurality of protruding structures are integrally formed. The one or more surfaces including the plurality of protruding structures are formed by an additive manufacturing process. The plurality of protruding structures include a plurality of needles. Optionally, the plurality of protruding structures include a plurality of needles that are disposed substantially perpendicular to the body portion. Alternatively, the plurality of protruding structures include a plurality of needles that are disposed at an angle to the body portion. Preferably, the plurality of protruding structures include a plurality of needles that include titanium. The body portion defines a hollow interior cavity. Optionally, the body portion defines one or more ports that are configured to receive a bone screw. The body portion defines one or more ports that are configured to allow bony ingrowth.

In a further exemplary embodiment, the present invention provides a surgical implant device, including: an implant body; a porous layer disposed adjacent to the implant body, wherein the porous layer includes a lattice of intersecting struts; and a plurality of needle structures protruding from the porous layer opposite the implant body, wherein at least some of the plurality of needle structures traverse the porous layer and are anchored to the implant body. The plurality of needle structures that traverse the porous layer and are anchored to the implant body are coupled to one or more intersecting struts of the lattice. Optionally, some of the plurality of needle structures are spaced apart from the implant body and are anchored only to the porous layer. Preferably, one or more of the implant body, the porous layer, and the plurality of needle structures are formed by an additive manufacturing technique. Optionally, one or more of the implant body, the porous layer, and the plurality of needle structures include a titanium material. The intersecting struts of the lattice have a plurality of thicknesses, lengths, cross-sectional shapes, and intersection points. Optionally, the plurality of needle structures are disposed substantially normal to a surface of the implant body. Optionally, the plurality of needle structures are disposed randomly across a surface of the implant body. The plurality of needle structures are disposed across the surface of the implant body with a density of about 0.3 needles/mm$^2$.

Optionally, each of the plurality of needle structures has a substantially rectangular cross-sectional shape.

In a still further exemplary embodiment, the present invention provides a method for manufacturing a surgical implant device, including: providing an implant body; disposing a porous layer adjacent to the implant body, wherein the porous layer includes a lattice of intersecting struts; and providing a plurality of needle structures protruding from the porous layer opposite the implant body, wherein at least some of the plurality of needle structures traverse the porous layer and are anchored to the implant body. The plurality of needle structures that traverse the porous layer and are anchored to the implant body are coupled to one or more intersecting struts of the lattice. Optionally, some of the plurality of needle structures are spaced apart from the implant body and are anchored only to the porous layer. Preferably, the providing, disposing, and providing steps include, using a software application: defining a melt volume corresponding to a volume occupied by the implant body; defining a structure volume corresponding to a volume occupied by the porous layer; defining a needle volume corresponding to a volume occupied by the plurality of needle structures; formulating a lattice pattern within the structure volume; formulating a needle pattern within the needle volume; and additively manufacturing one or more of the implant body, the porous layer using the lattice pattern, and the plurality of needle structures using the needle pattern. The intersecting struts of the lattice have a plurality of thicknesses, lengths, cross-sectional shapes, and intersection points. Optionally, the plurality of needle structures are disposed substantially normal to a surface of the implant body. Optionally, the plurality of needle structures are disposed randomly across a surface of the implant body. The plurality of needle structures are disposed across the surface of the implant body with a density of about 0.3 needles/mm$^2$. Optionally, each of the plurality of needle structures has a substantially rectangular cross-sectional shape. The method for manufacturing the surgical implant device further includes surface treating a bone opposition surface of one or more of the implant body, the porous layer, and the plurality of needle structures.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Figure 1:
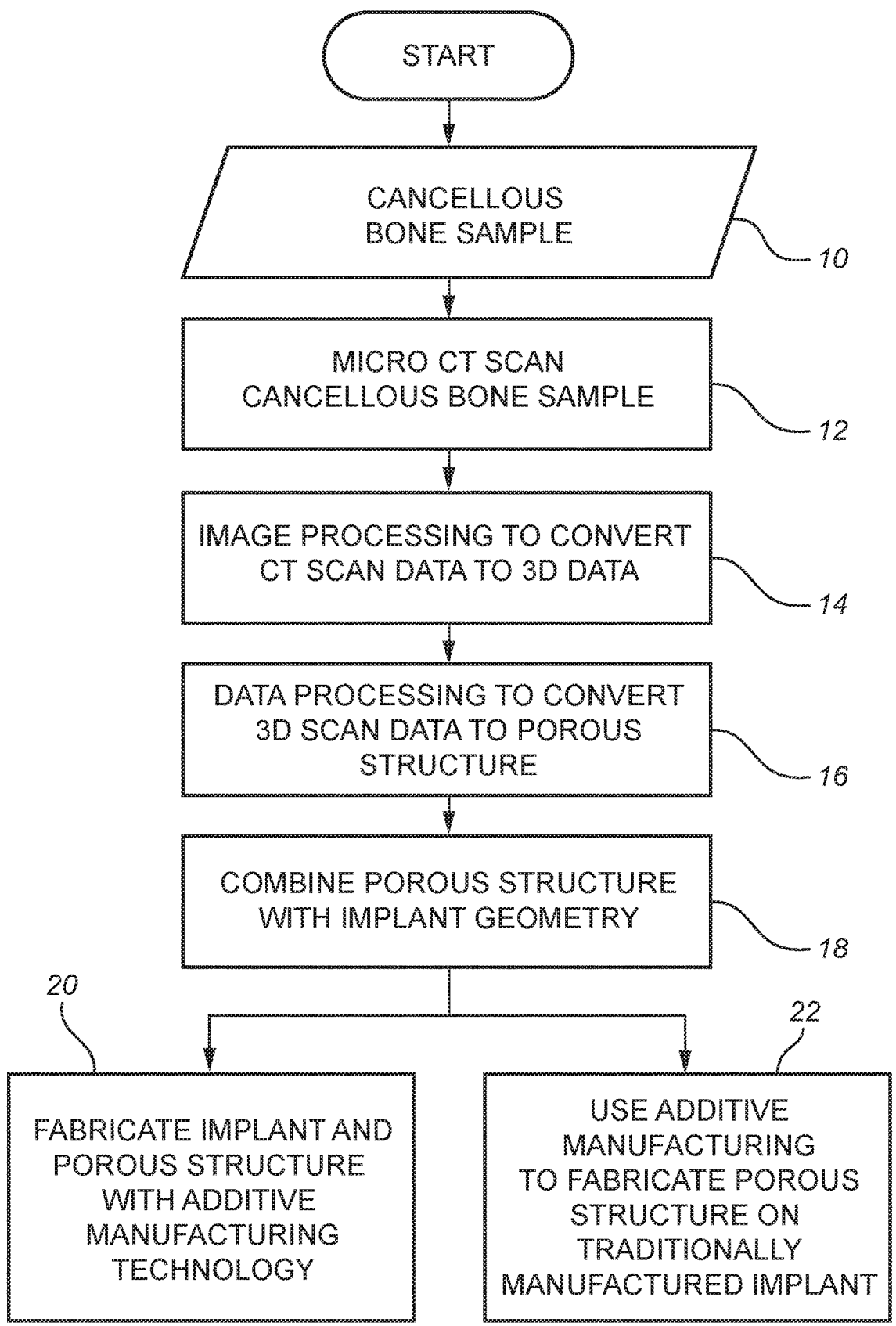
FIG. 1 depicts an exemplary method for producing surgical implant devices having osteo-derived and/or osteo-porous surface(s).

Generally speaking, and without intending to be limiting, one aspect of the invention relates to improved medical implants that include, for example, at least the following: a primary structure formed from metal; and at least one needle-populated, metallic surface portion formed on at least one exterior portion of the primary structure, the at least one surface portion located such that it engages with a patient's bone when the implant is implanted in the patient. Such needle-populated, metallic surface portions may contain, for example, a collection of at least fifty, a hundred, two hundred, five-hundred or more needles, and may be further characterized by at least one, two, three, four, five or more of the following characteristics: (a) the needles in the collection are all oriented substantially normal to the surface portion; (b) the needles in the collection are all oriented in substantially the same direction, with the direction being other than normal to the surface portion; (c) the needles in the collection are all oriented in substantially the same direction, with the direction being other than normal to the surface portion, but within 15 degrees from the normal direction; (d) the needles in the collection are all oriented in substantially the same direction, with the direction being other than normal to the surface portion, and more than 15 degrees from the normal direction; (e) the collection includes needles oriented in at least three different directions relative to the surface portion; (f) the collection includes needles oriented in at least five different directions relative to the surface portion, with all of the needles oriented within 20 degrees from the surface portion normal direction; (g) all of the needles in the collection have substantially the same height; (h) the collection includes needles of at least three different heights; (i) all of the needles in the collection have substantially the same shape; (j) the collection includes needles of at least two different shapes; (k) the needles are distributed substantially uniformly over the surface portion; (l) the needles are distributed non-uniformly over the surface portion; (m) all of the needles in the collection are anchored to the primary structure; (n) most of the needles in the collection are anchored to the primary structure; (o) most of the needles in the collection are anchored to structural elements contained within an osteo-porous, osteo-derived or trabecular coating on the at least one exterior portion of the primary structure; and/or (p) all of the needles in the collection are anchored to structural elements contained within an osteo-porous, osteo-derived or trabecular coating on the at least one exterior portion of the primary structure. The at least one exterior portion preferably includes at least one osteo-porous surface, which may comprise at least one osteo-derived surface. The at least one osteo-porous surface and the needles may be simultaneously formed by an additive manufacturing process, such as, but not limited to, EBM or DMSLS. The primary structure may comprise, for example, a dental implant, a foot-and-ankle or long-bone osteotomy wedge, an intervertebral fusion device, a tibial/femoral augment or spacer, a tibial tray portion of a knee implant, a femoral component portion of a knee implant, a primary hip implant, a revision hip implant, a hip trauma component, an acetabular cup, a hip acetabular augment, or other appropriate structure.

Again, generally speaking, and without intending to be limiting, another aspect of the invention relates to method(s) for making a medical implants with at least one osteo-porous surface by, for example: forming at least a portion of a primary structure of the implant; and forming at least one needle-populated, metallic surface portion on at least one exterior portion of the primary structure using an additive manufacturing technique, the at least one needle-populated surface portion located such that it engages with a patient's bone when the implant is implanted in the patient.

Other aspects of the invention relate to additional features, structures, processes and materials depicted in the figures and/or described herein.

Referring to FIG. 1, the exemplary flow starts with a spongy bone sample 10, which is micro CT scanned to obtain 3D scan data 12, which is then processed into solid model data representing an osteo-porous or osteo-derived texture 14,16. This texture data is then combined with data representing the overall implant geometry to create a fabrication file 18 for use by either of the manufacturing steps 20,22 that follow.

The fabrication file may utilize any recognizable solid model specification, such as ".amf" format or ".stl" format, and may be embodied on any sort of permanent storage medium (e.g., CD, CD-ROM, flash), semi-permanent (e.g., SRAM) or transitory (e.g., DRAM) storage medium, or embodied in a coded data signal.

Figure 1A:
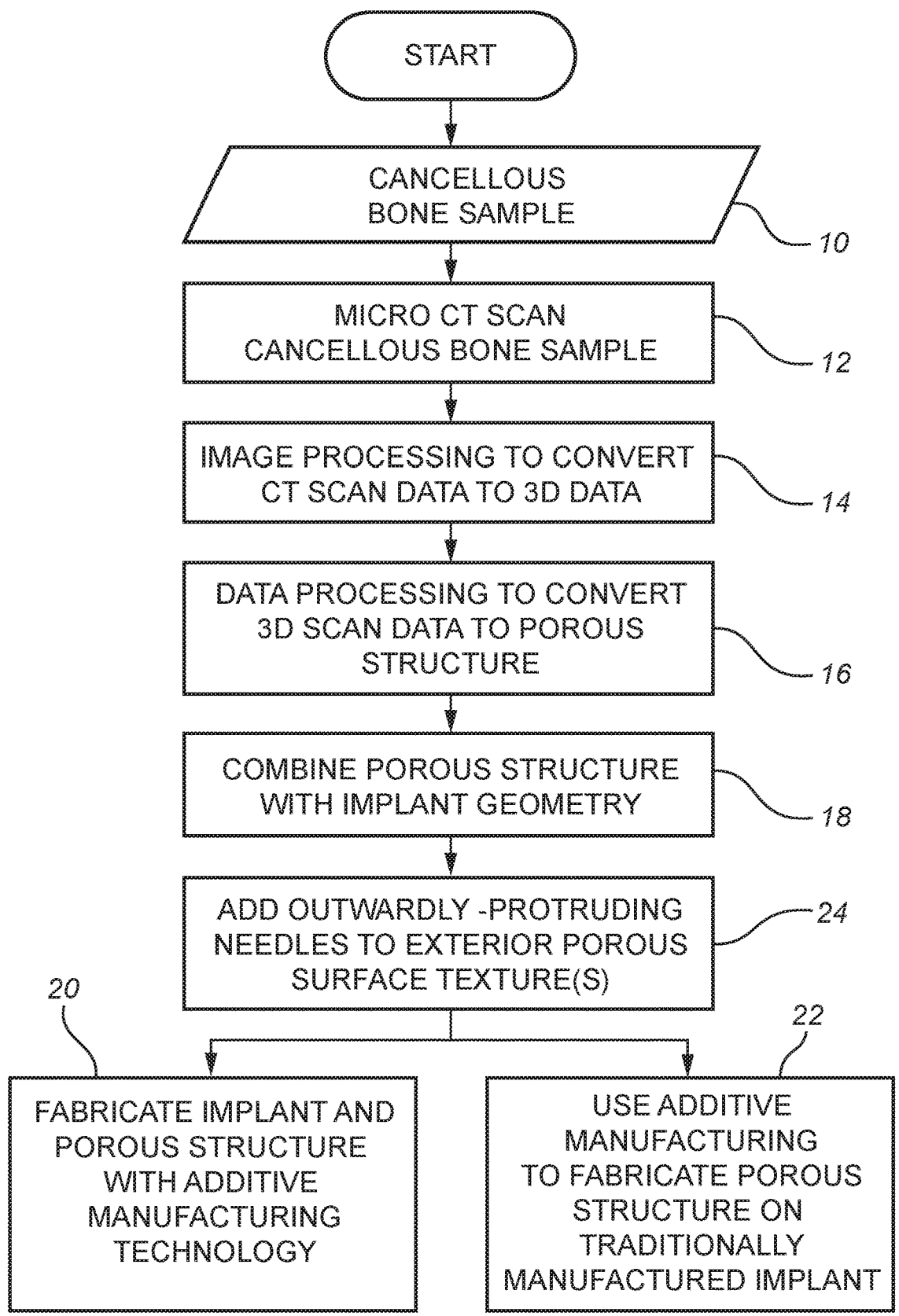
FIG. 1A depicts an exemplary method for producing surgical implant devices having osteo-derived and/or osteo-porous surface(s) with additional outwardly-protruding "needles."
Figure 1B:
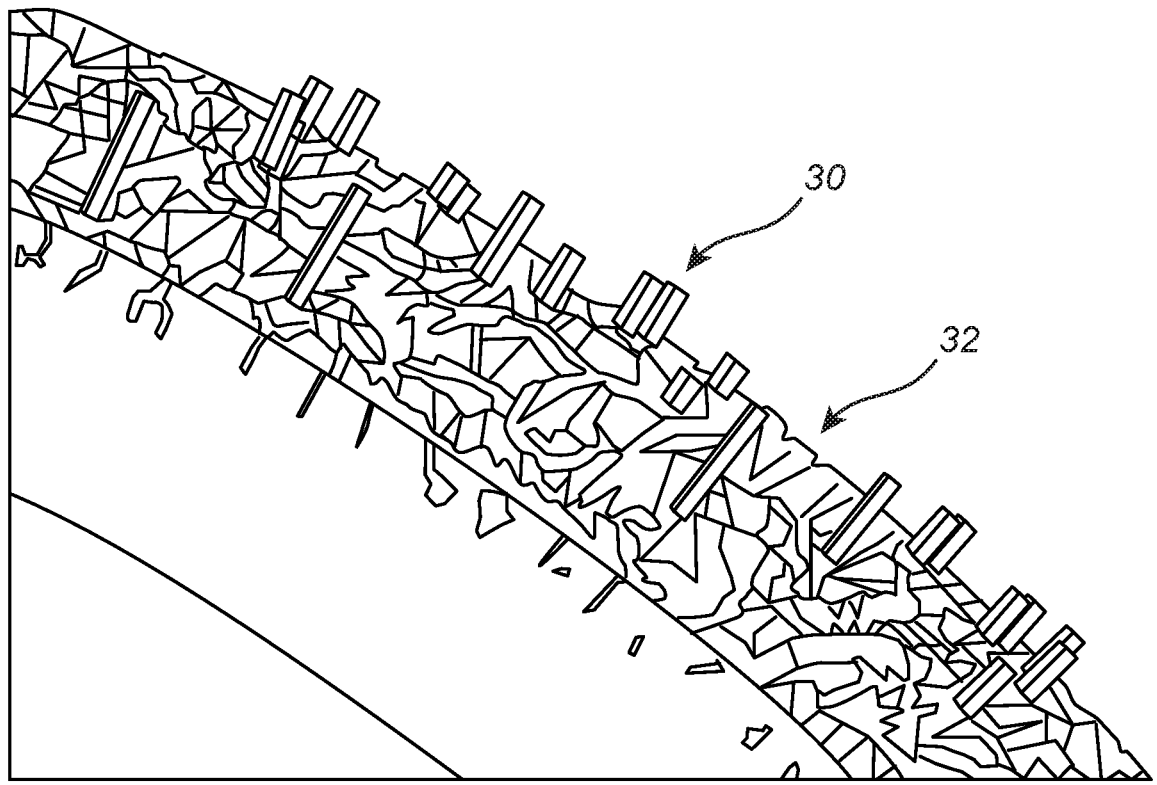
FIG. 1B depicts an exploded section of a computer-generated rendering of an exemplary osteo-derived and/or osteo-porous surface with outwardly-protruding needles.
Figure 1C:
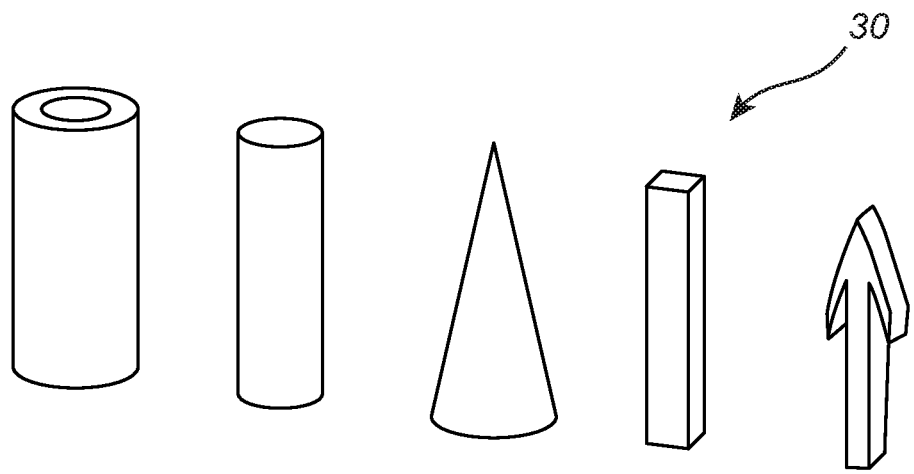
FIG. 1C conceptually depicts various exemplary shapes of outwardly-protruding needles (including, from left to right, tubular, rod-shaped, conical, square/rectangular, and barbed/irregular) useful with the present invention.

Referring to FIG. 1A, an additional step can be inserted that adds outwardly-protruding "needles" on the outer surface(s) of the osteo-porous and/or osteo-derived coating(s) 24. Referring to FIGS. 1B and 1C, such needles 30 substantially increase the coefficient of friction of the implant surface 32. Having a high coefficient of friction is clinically advantageous because it provides stronger initial fixation, which is important before bone is able to grow onto/into the porous structure. Such needles 30 can be uniformly or non-uniformly distributed along the porous surface. Likewise, various shapes for the needles 30 are possible, including rectangular, pyramidal, conical, tube-shaped, barbed, etc. Also, the needles 30 need not be oriented exactly normal to the exterior surface, but are preferably oriented in a substantially normal (e.g., within +/−15 degrees from normal) orientation. Furthermore, the orientation and/or shape of all needles 30 need not be the same, and the needles 30 may be rendered on selected portions, or the entirety, of the exterior coated surface(s).

Figure 1D:
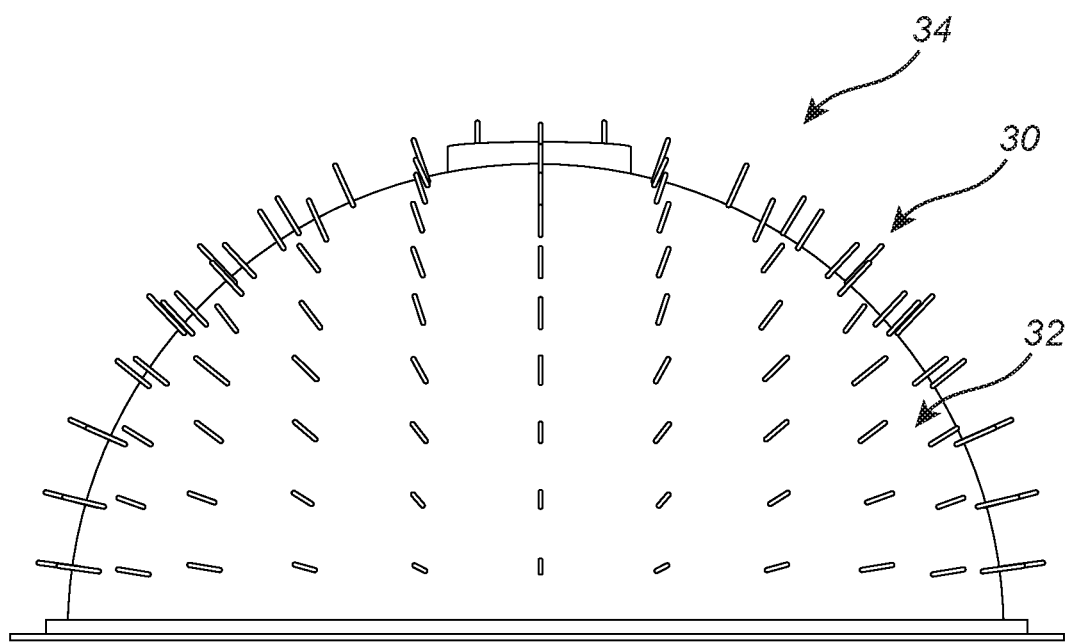
FIG. 1D conceptually depicts an exemplary surgical implant device surface containing a uniform distribution of outwardly-protruding needles.
Figure 1E:
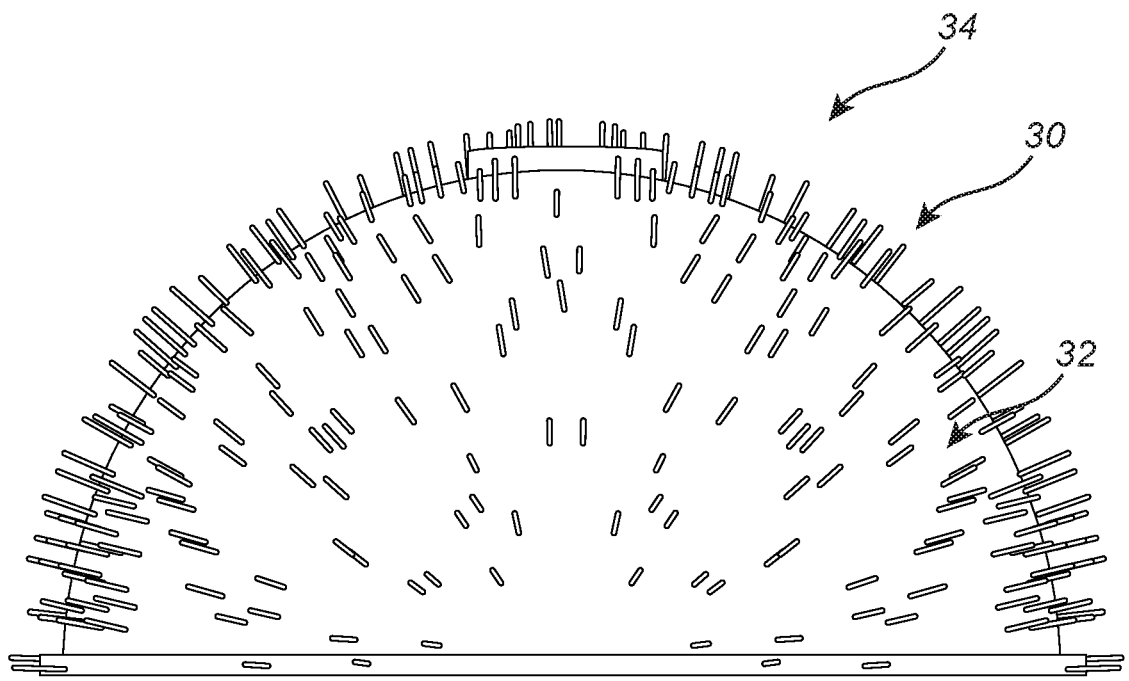
FIG. 1E conceptually depicts an exemplary surgical implant device surface containing a non-uniform distribution of outwardly-protruding needles.
Figure 1F:
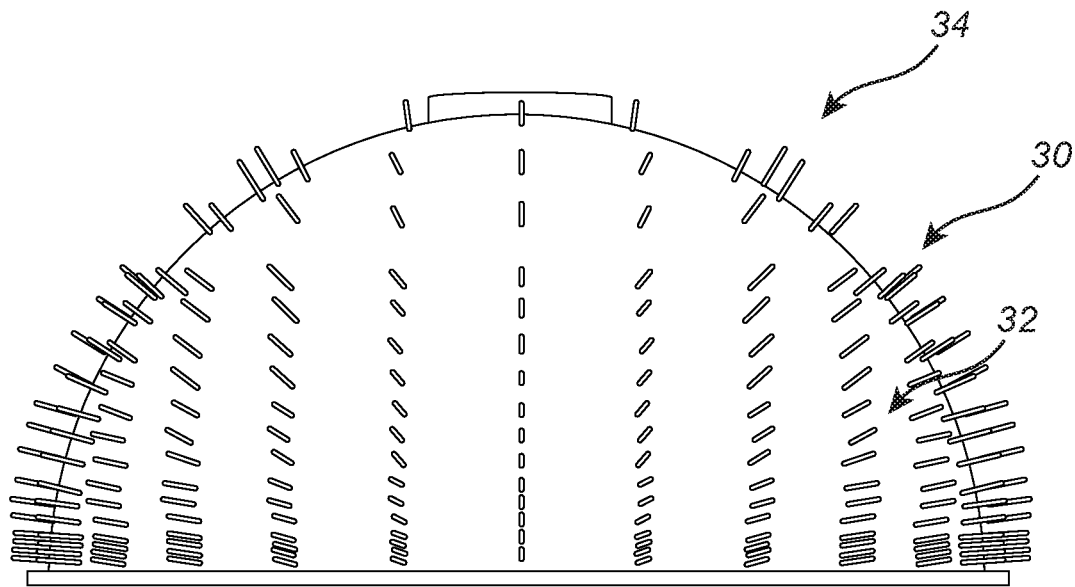
FIG. 1F conceptually depicts an exemplary surgical implant device surface containing a gradient distribution of outwardly-protruding needles.
Figure 1G:
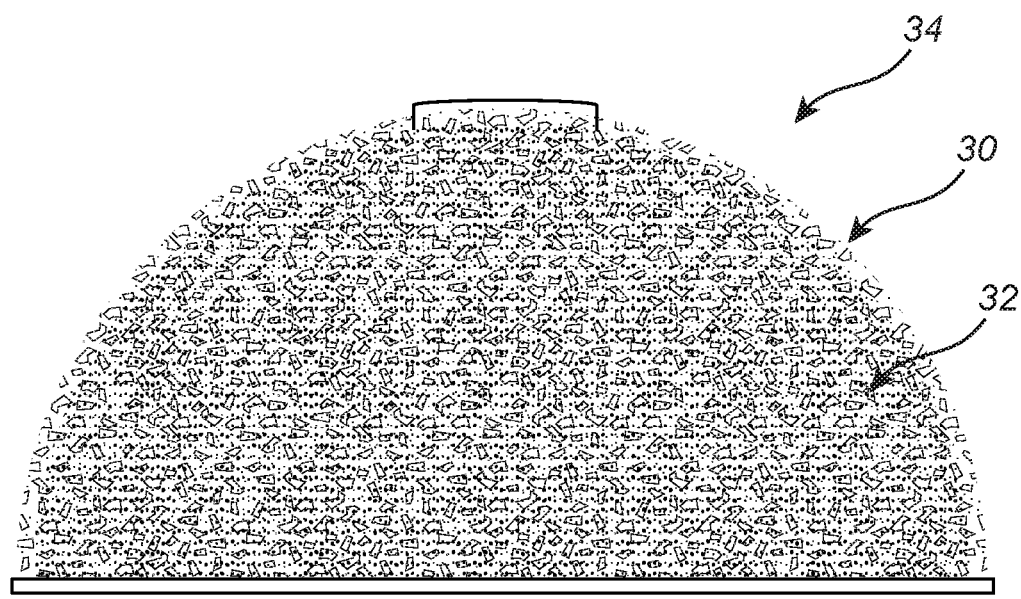
FIG. 1G conceptually depicts an exemplary osteo-porous, osteo-derived, and/or trabecular surgical implant device surface containing a randomized distribution of outwardly-protruding needles.

FIG. 1D conceptually depicts an exemplary surgical implant device surface, specifically an acetabular cup 34, containing a uniform distribution of outwardly-protruding needles 30 disposed on a surface 32 thereof. FIG. 1E conceptually depicts an exemplary surgical implant device surface, specifically an acetabular cup 34, containing a non-uniform distribution of outwardly-protruding needles 30 disposed on a surface 32 thereof. FIG. 1F conceptually depicts an exemplary surgical implant device surface, specifically an acetabular cup 34, containing a gradient distribution of outwardly-protruding needles 30 disposed on a surface 32 thereof. FIG. 1G conceptually depicts an exemplary surgical implant device surface, specifically an acetabular cup 34, containing a randomized distribution of outwardly-protruding needles 30 disposed on a surface 32 thereof.

Figure 1H:
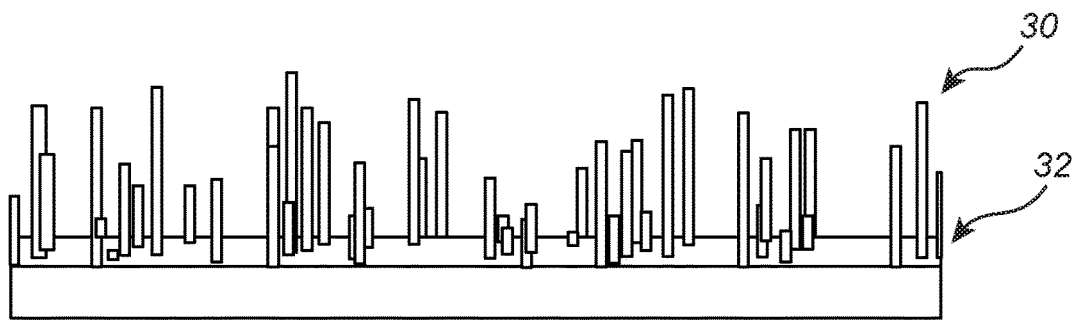
FIG. 1H conceptually depicts an exemplary cross-section of an implant surface containing a randomized distribution of needle heights.
Figure 1I:
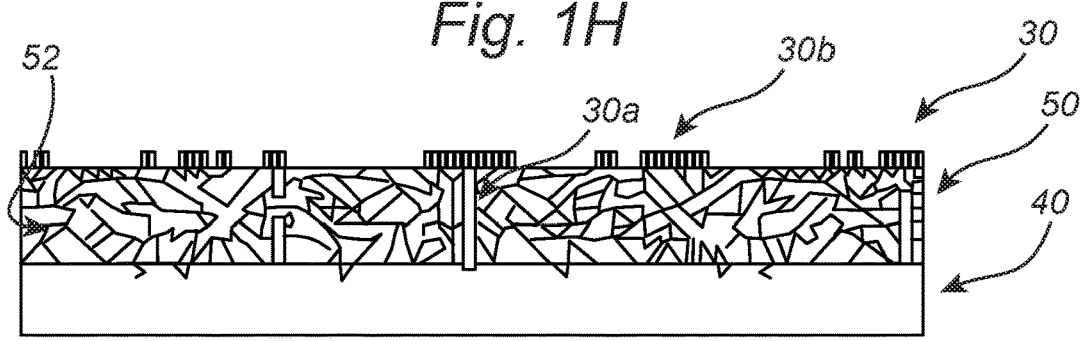
FIG. 1I conceptually depicts an exemplary cross-section of an implant surface containing an exemplary osteo-porous, osteo-derived, and/or trabecular coating with needles anchored to the underlying substrate.

FIGS. 1H and 1I conceptually depict an exemplary cross-section of a generic implant surface 32 containing a randomized distribution of needles 30. FIG. 1H illustrates that this collection of needles 30 can be randomized in terms of distribution and/or needle length/height with respect to the implant surface 32.

Referring specifically to FIG. 1I, the methodology and implant of the present invention generate and provide a surface 32 that includes the implant body 40 and a porous layer 50 that is disposed directly adjacent to the implant body 40. The porous layer 50 can be additively manufactured on top of the implant body 40, or can be additively manufactured with the implant body 40. The porous layer 50 consists of a bone-interfacing lattice of macroscopic, randomly distributed stochastic struts 52 of various thicknesses, shapes, and intersection points. This lattice is comparable to cancellous bone in terms of pore size and overall porosity, thus it elicits a favorable bone response when applied to the bone-opposition surfaces of the associated implant to which it is applied. The needles 30 are additively manufactured with the porous layer 50 and/or the implant body 50 and some or all of the needles 30a protrude from and are anchored directly to the implant body 40, through the porous layer 50, and from the bone-opposition surface of the porous layer 50, forming regularly or randomly-arranged friction structures protruding from the bone-opposition surface of the porous layer 50. This provides advantageous needle strength and stability. Within the porous layer 50, these penetrating needles 30a are integrally formed with or otherwise anchored to adjacent of the struts of the lattice, again providing advantageous needle strength and stability. In one preferred embodiment, all needles 30 are planted 0.004-0.006 in. into the solid substrate, either physically or for behavioral modeling purposes (having a corresponding support stiffness), and extend about 0.008 in. above the bone-opposition surface of the porous layer 50, with a plurality of intervening lattice strut connections along the length of each needle 30. Here, the needles are 0.2 mm×0.2 mm rectangular prisms with constant cross-sections. The preferred needle density is 0.3 needles/mm$^2$ or 1 needle every 3.33 mm$^2$ for optimal bone friction engagement. The needles 30 are largely disposed normal to the bone-opposition surface of the porous layer 50 and the implant body 40, but may be angled with respect to one another due to curvature of the bone-opposition surface of the porous layer 50 and the implant body 40. The finished porous layer-needle construct is blasted with calcium phosphate or otherwise surface treated to promote roughness of the resulting bone-engagement structure.

Figure 1J:
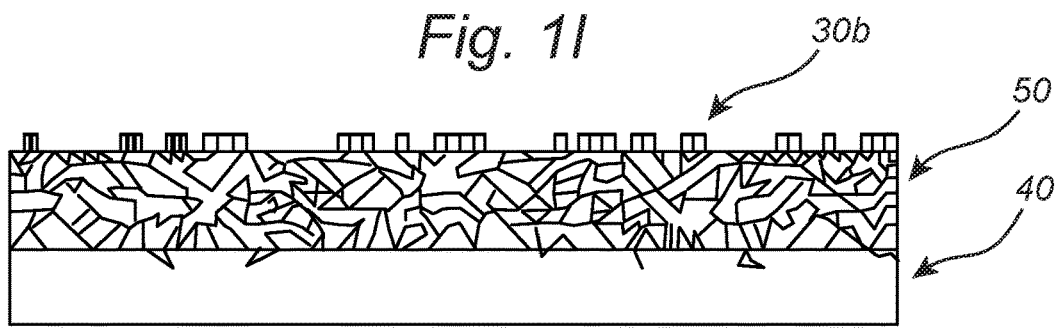
FIG. 1J conceptually depicts an exemplary cross-section of an implant surface containing an exemplary osteo-porous, osteo-derived, and/or trabecular coating with needles anchored to the osteo-porous, osteo-derived, and/or trabecular coating.
Figure 1K:
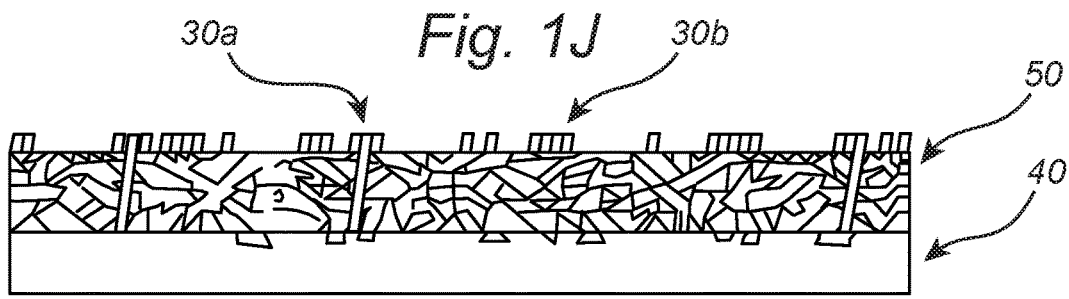
FIG. 1K conceptually depicts an exemplary cross-section of an implant surface containing an exemplary osteo-porous, osteo-derived, and/or trabecular coating with uniformly tilted needles anchored to the underlying substrate.
Figure 1L:
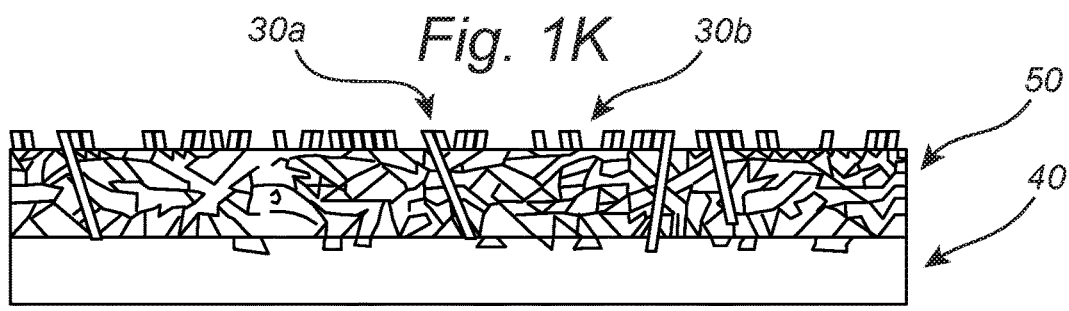
FIG. 1L conceptually depicts an exemplary cross-section of an implant surface containing an exemplary osteo-porous, osteo-derived, and/or trabecular coating with non-uniformly tilted needles anchored to the underlying substrate.

FIG. 1J conceptually depicts an exemplary cross-section of an implant surface containing an exemplary osteo-porous, osteo-derived, and/or trabecular coating 50 with needles 30b anchored only to the bone-opposition surface of the osteo-porous, osteo-derived, and/or trabecular coating 50 and not the underlying implant body 40. FIG. 1K conceptually depicts an exemplary cross-section of an implant surface containing an exemplary osteo-porous, osteo-derived, and/or trabecular coating 50 with uniformly tilted needles 30a, 30b variously anchored to both the bone-opposition surface of the osteo-porous, osteo-derived, and/or trabecular coating 50 and the underlying implant body 40. FIG. 1L conceptually depicts an exemplary cross-section of an implant surface containing an exemplary osteo-porous, osteo-derived, and/or trabecular coating 50 with non-uniformly tilted needles 30a,30b variously anchored to both the bone-opposition surface of the osteo-porous, osteo-derived, and/or trabecular coating 50 and the underlying implant body 40. Utilizing these or similar techniques, one can efficiently and advantageously form (and/or finish) implants of the sort depicted herein.

Figure 2A:
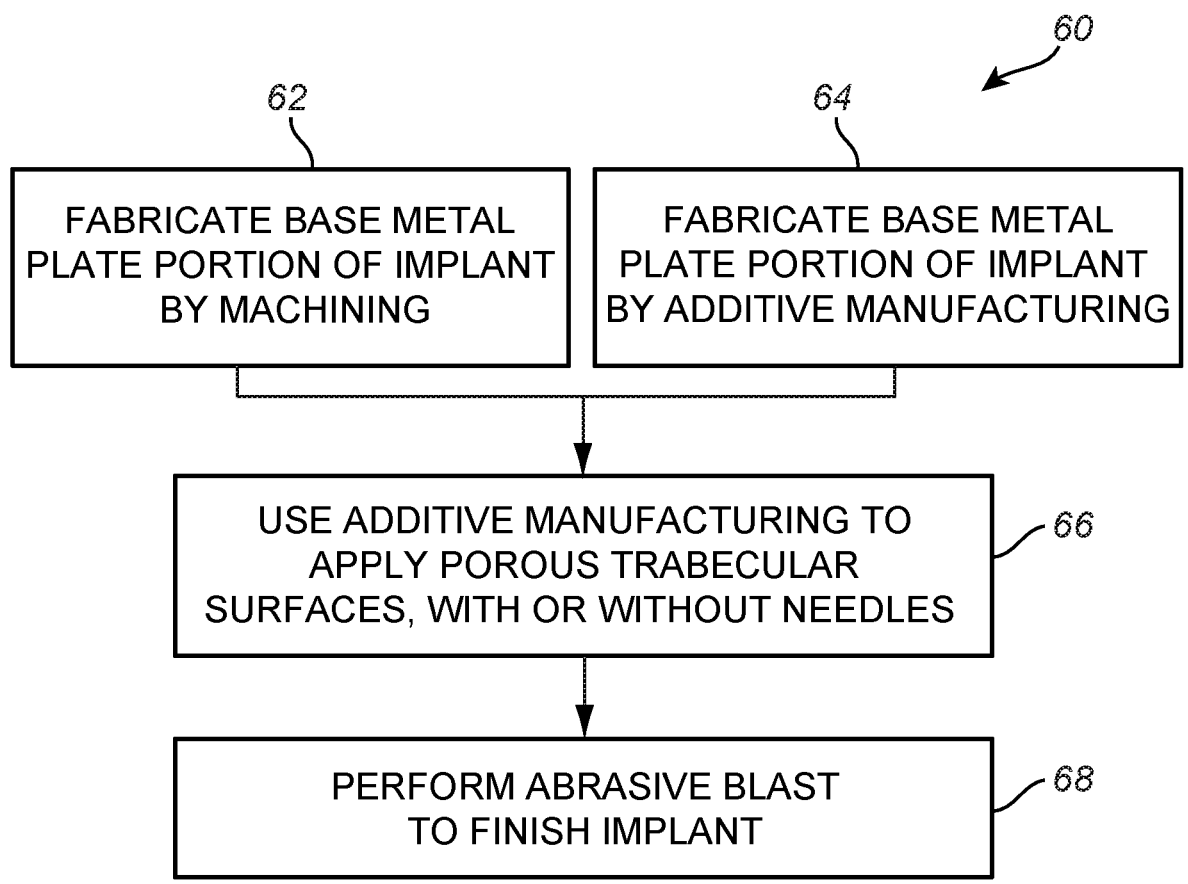
FIG. 2A depicts preferred process flows for manufacturing abrasive-blasted implants in accordance with the invention.
Figure 2B:
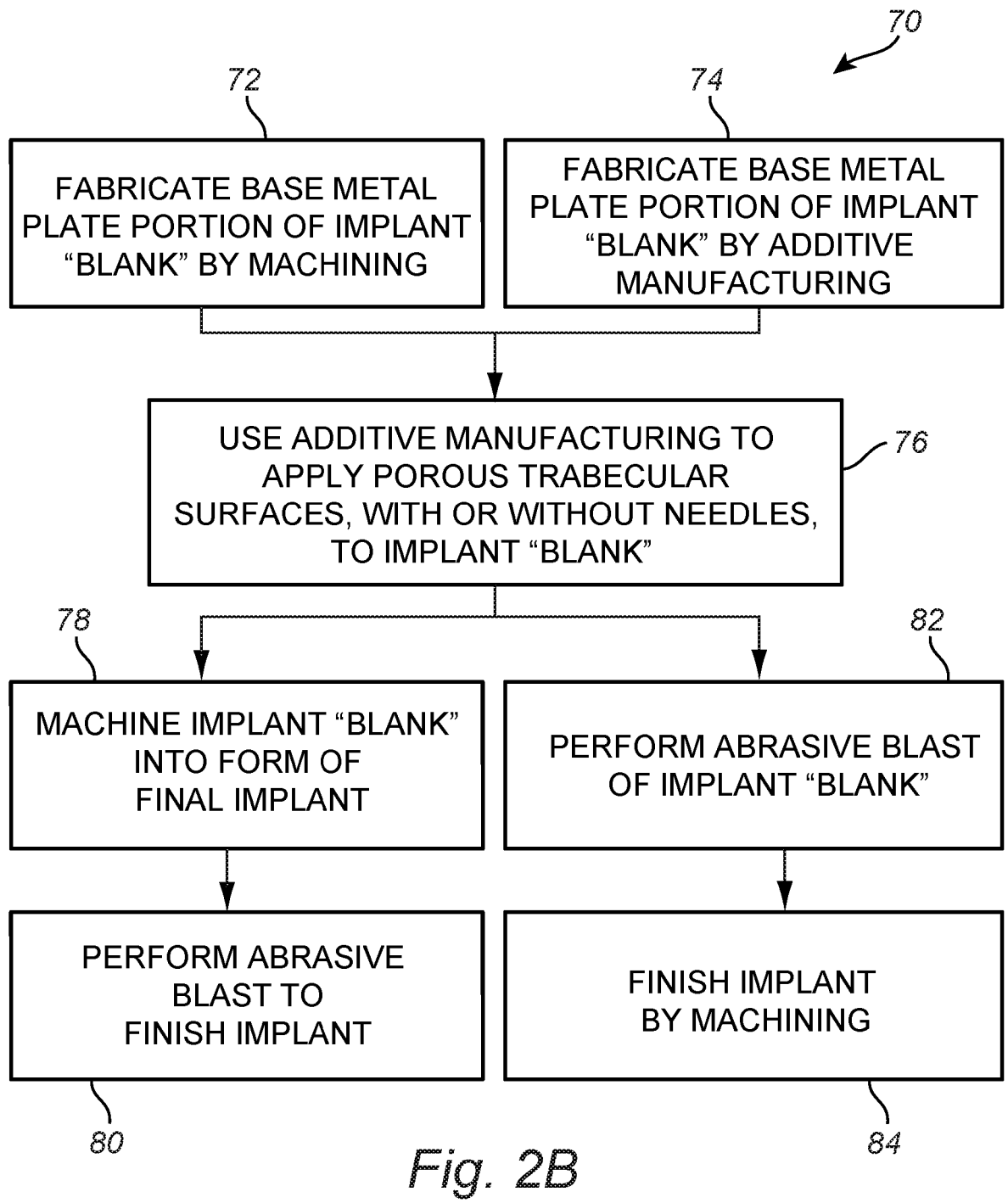
FIG. 2B depicts alternative process flows for manufacturing abrasive-blasted implants in accordance with the invention.
Figure 3A:
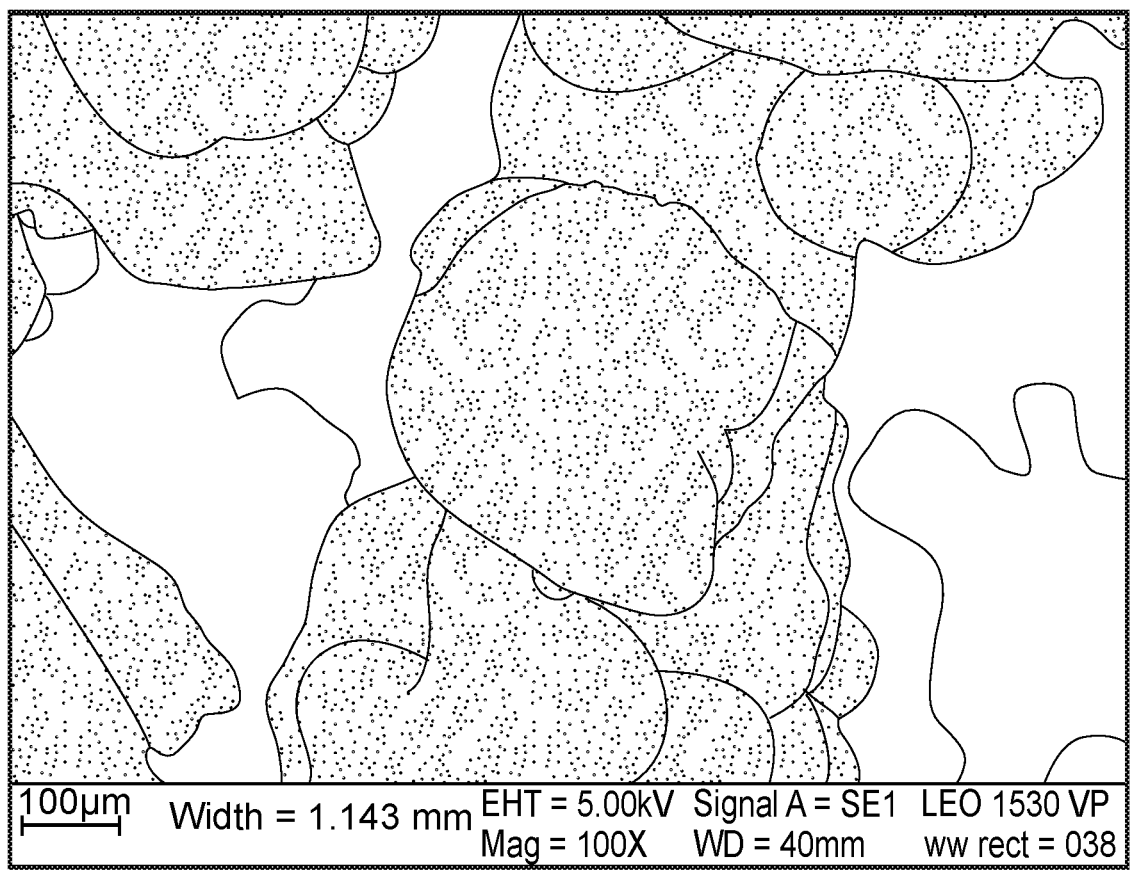
FIGS. 3A and 3B depict exemplary SEM views of porous/trabecular metal sections fabricated by additive manufacturing in accordance with the invention, but not subjected to a post-fabrication abrasive blast step.
Figure 3B:
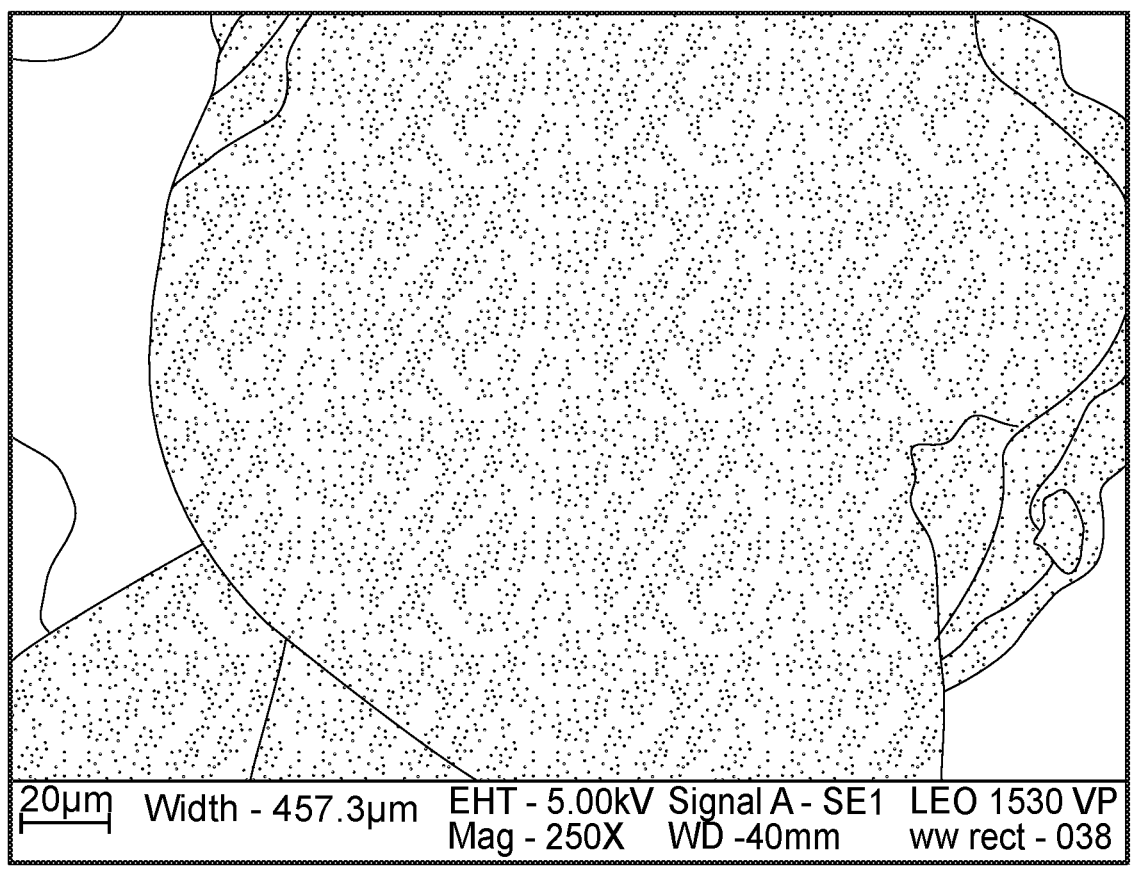
Figure 4A:
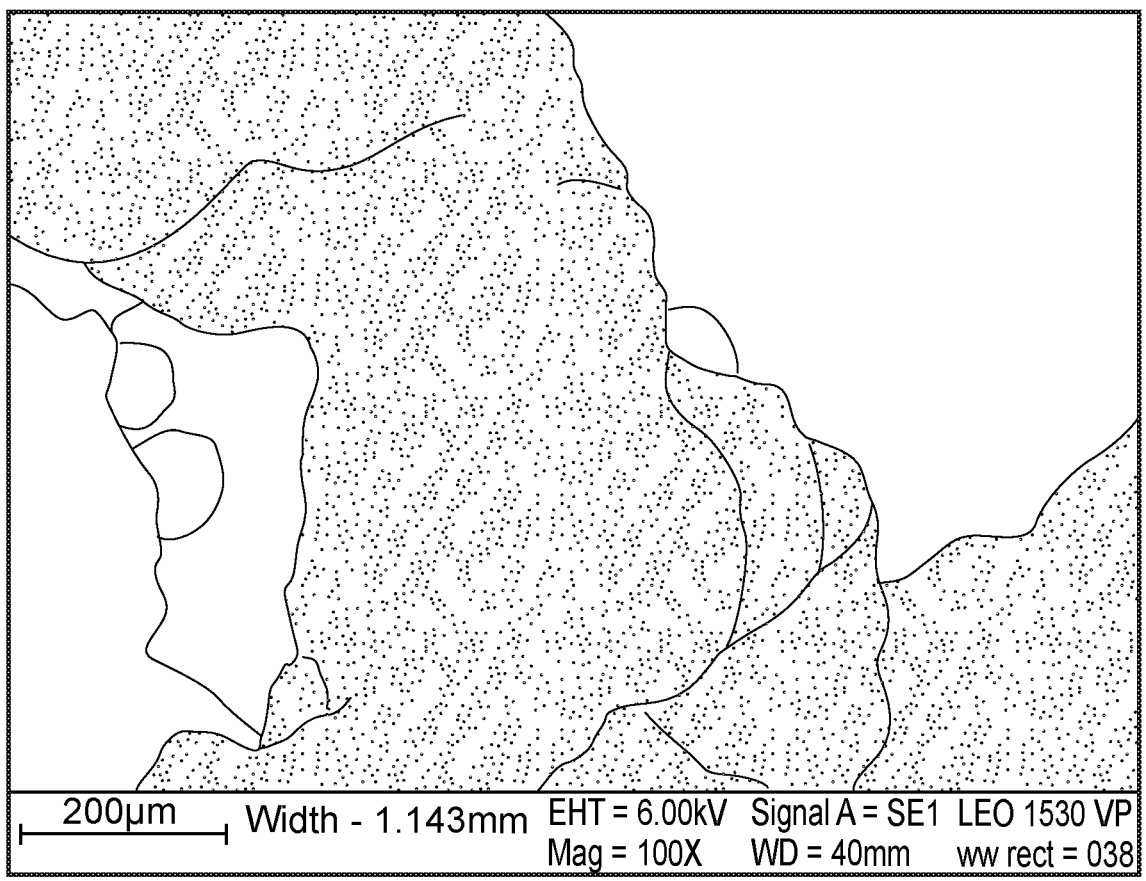
FIGS. 4A and 4B depict exemplary SEM views of porous/trabecular metal sections fabricated by additive manufacturing in accordance with the invention, after being subjected to a post-fabrication abrasive blast step.
Figure 4B:
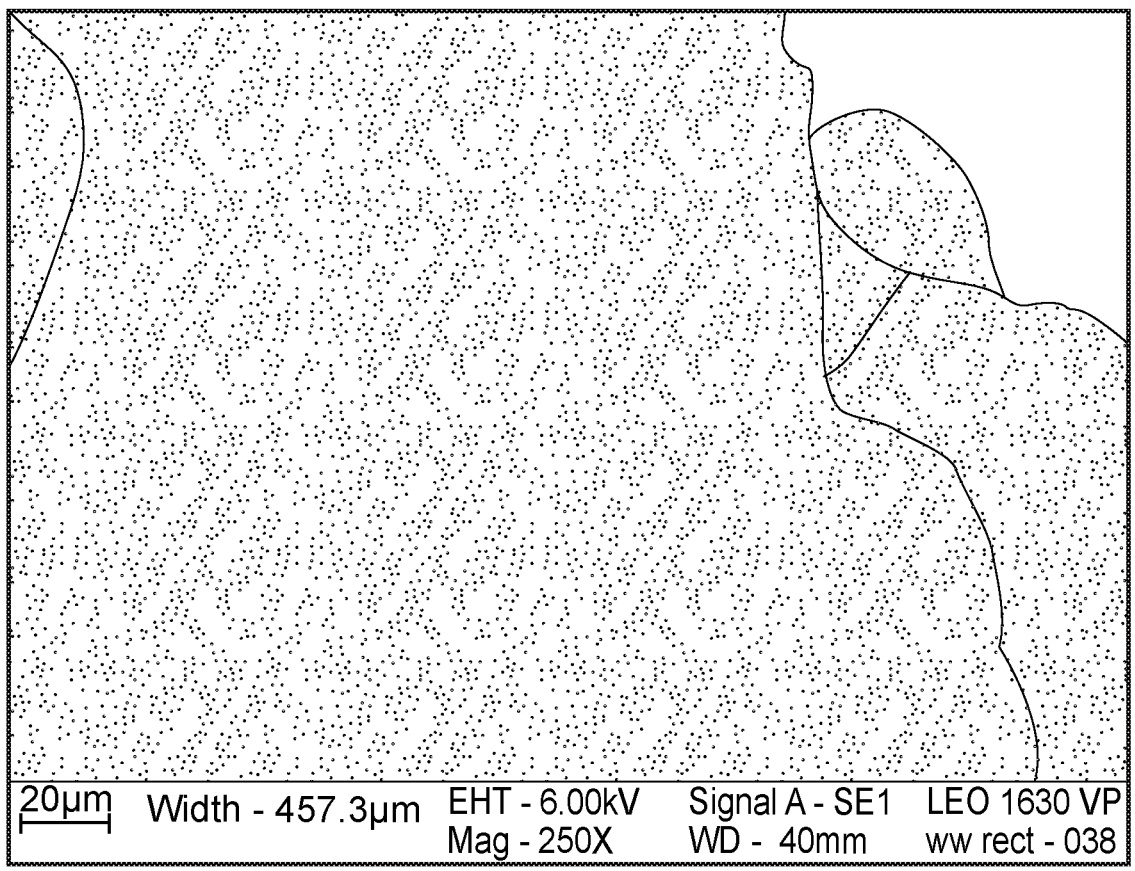
Figure 5A:
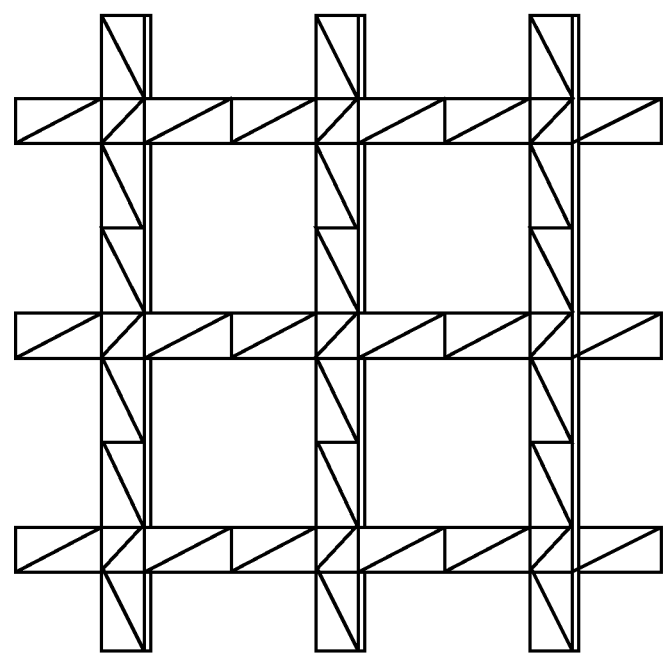
FIG. 5A conceptually depicts a 2-D rendering of a cubic lattice structure, with no node perturbation and no strut size randomization.
Figure 5B:
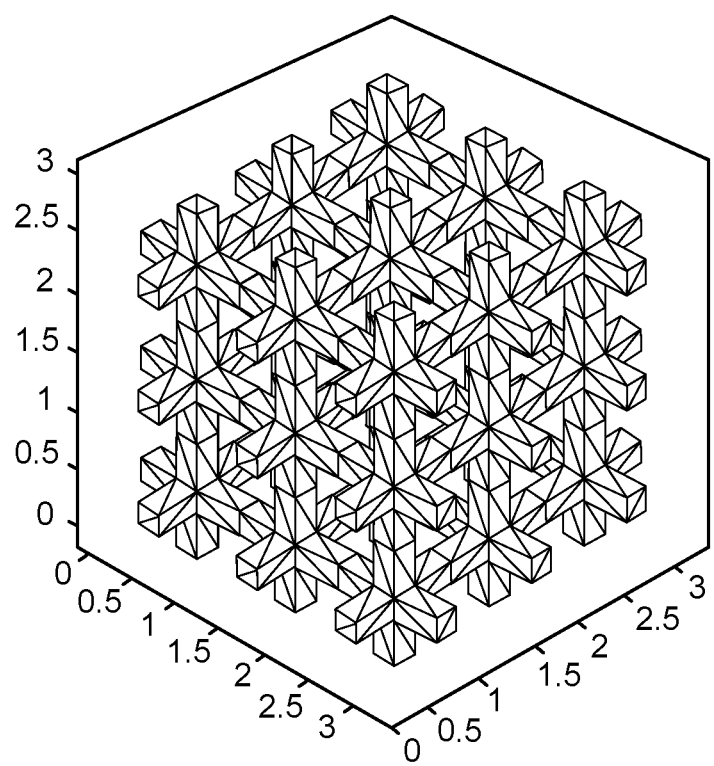
FIG. 5B conceptually depicts a 3-D rendering of the cubic lattice structure, with no node perturbation and no strut size randomization.
Figure 5C:
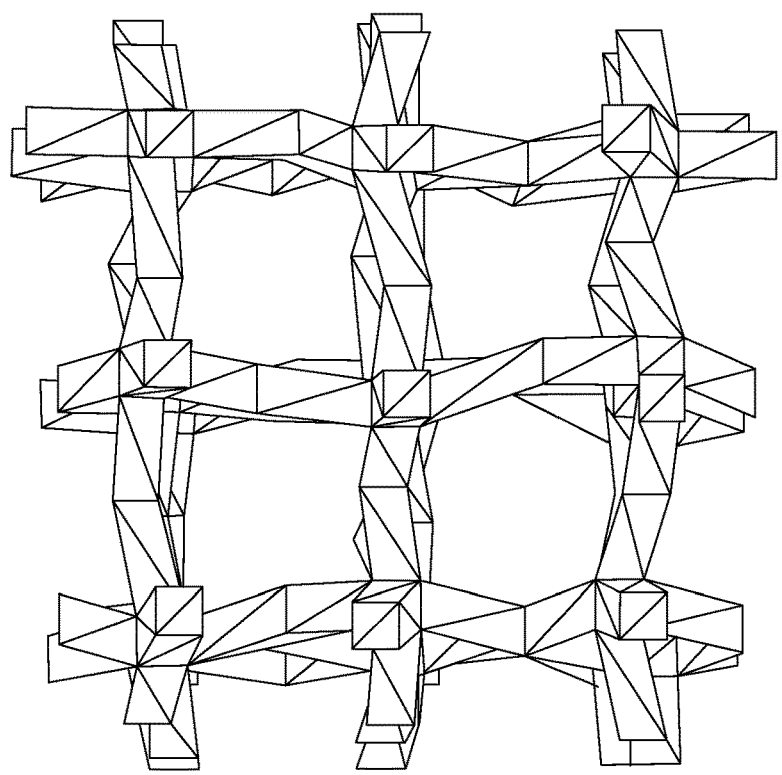
FIG. 5C conceptually depicts a 2-D rendering of a cubic lattice structure, with 20% node perturbation and no strut size randomization.
Figure 5D:
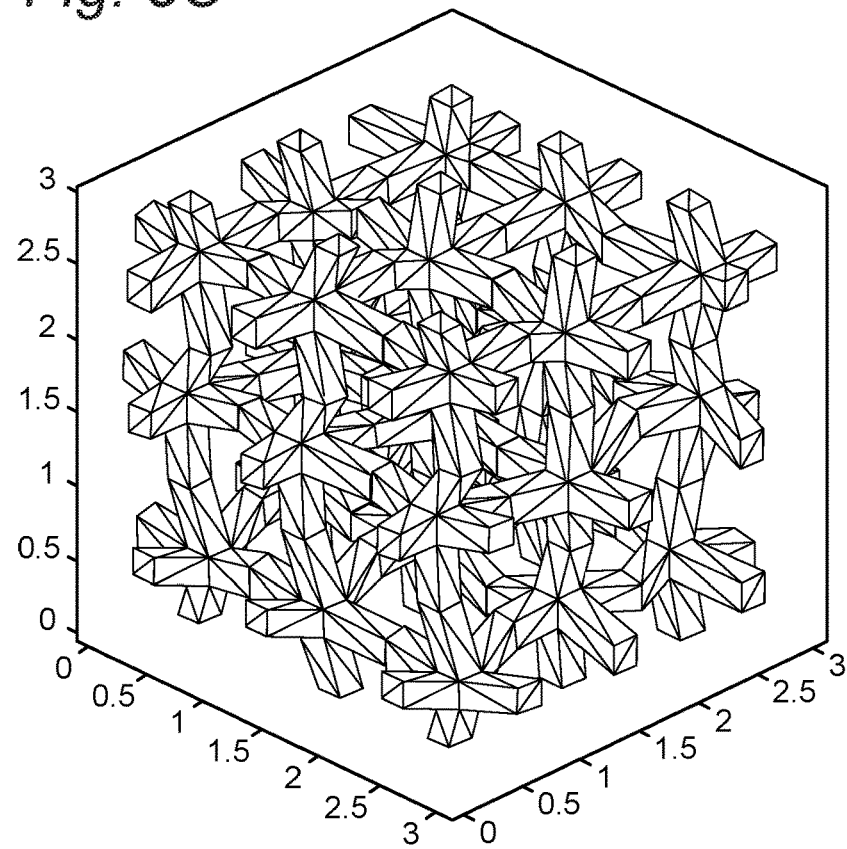
FIG. 5D conceptually depicts a 3-D rendering of the cubic lattice structure, with 20% node perturbation and no strut size randomization.
Figure 5E:
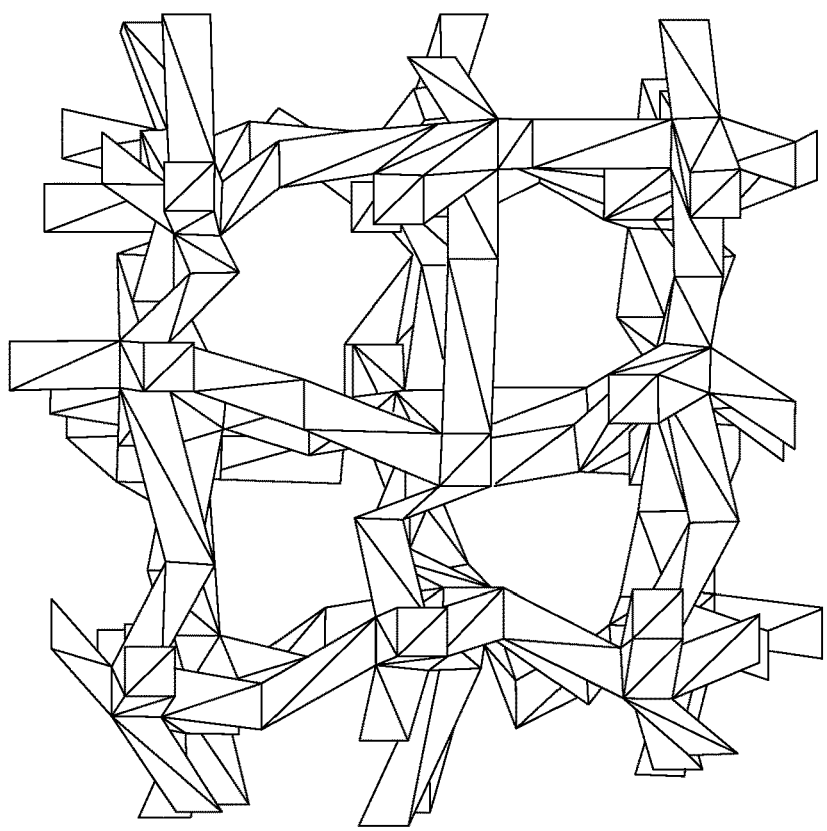
FIG. 5E conceptually depicts a 2-D rendering of a cubic lattice structure, with 40% node perturbation and no strut size randomization.
Figure 5F:
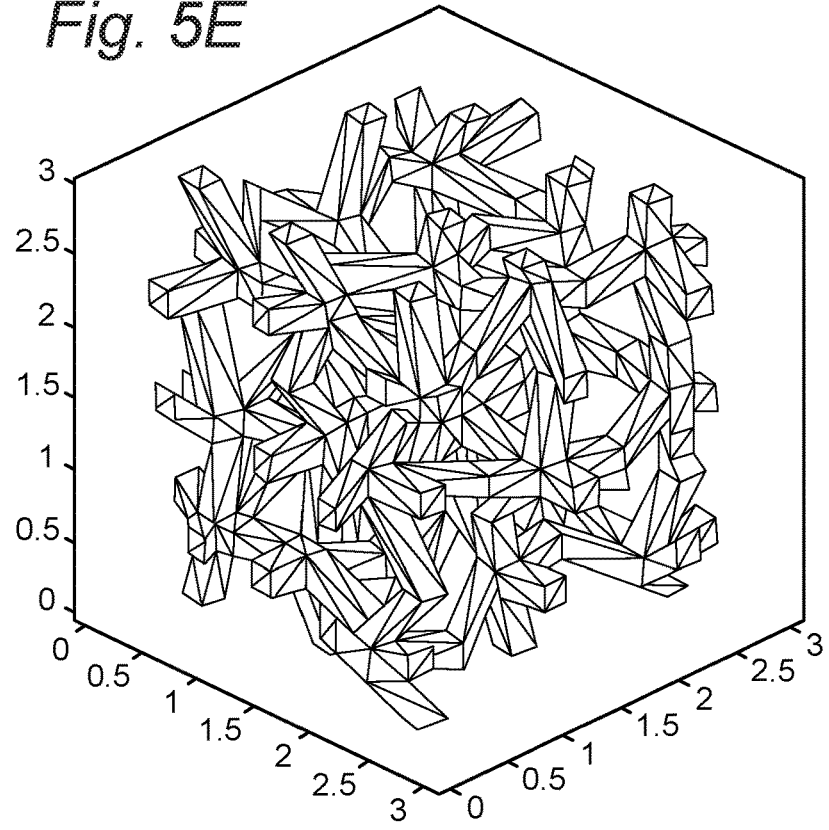
FIG. 5F conceptually depicts a 3-D rendering of the cubic lattice structure, with 40% node perturbation and no strut size randomization.
Figure 5G:
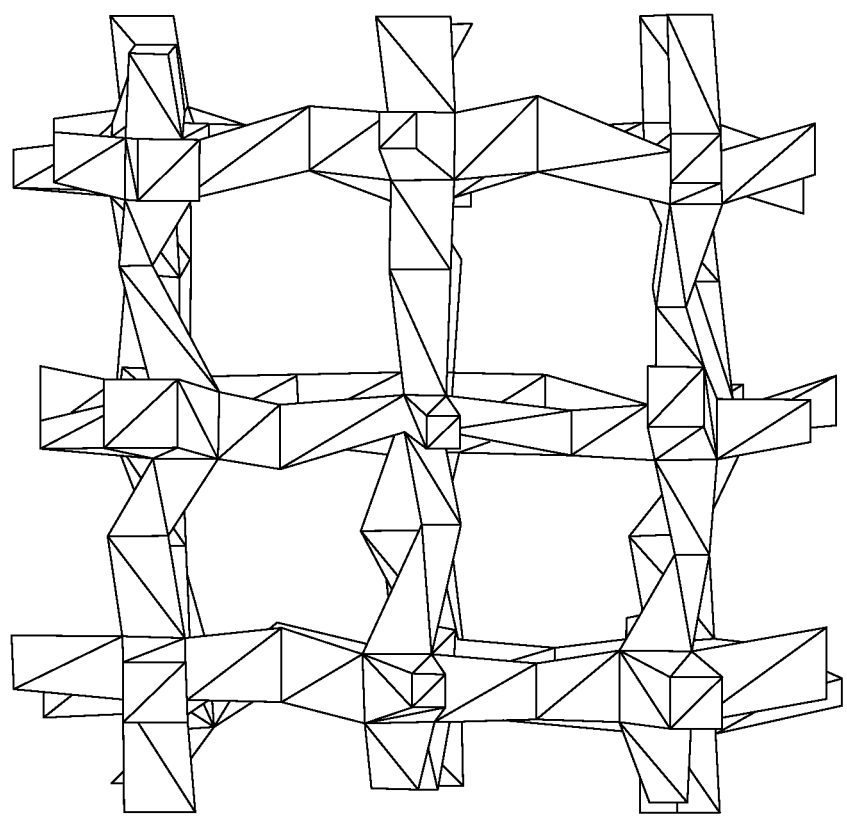
FIG. 5G conceptually depicts a 2-D rendering of a cubic lattice structure, with 20% node perturbation and 100% strut size randomization.
Figure 5H:
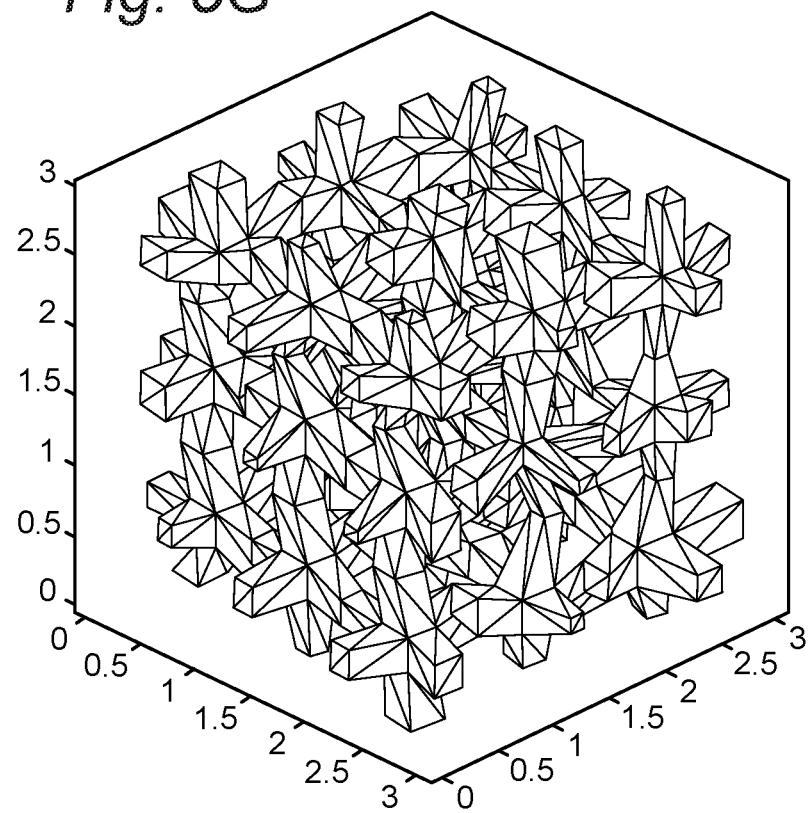
FIG. 5H conceptually depicts a 3-D rendering of the cubic lattice structure, with 20% node perturbation and 100% strut size randomization.
Figure 5I:
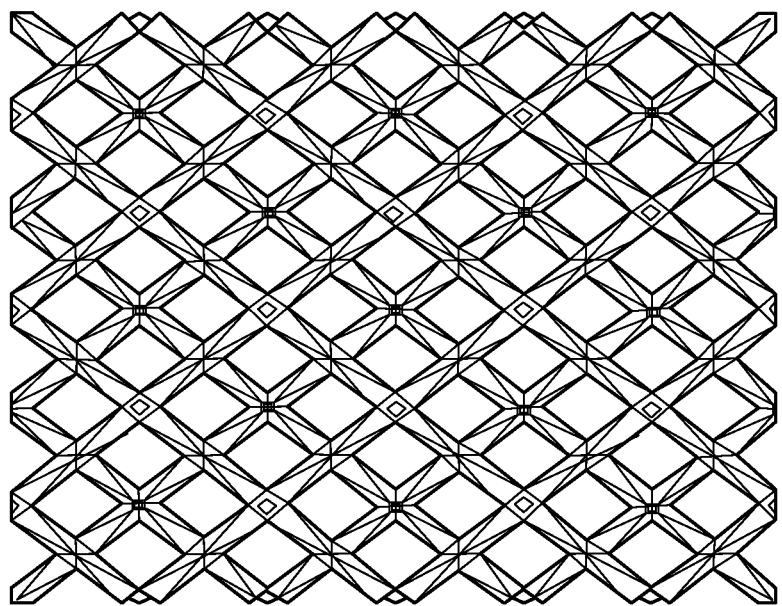
FIG. 5I conceptually depicts a 2-D rendering of a dodecahedron lattice structure, with no node perturbation and no strut size randomization.
Figure 5J:
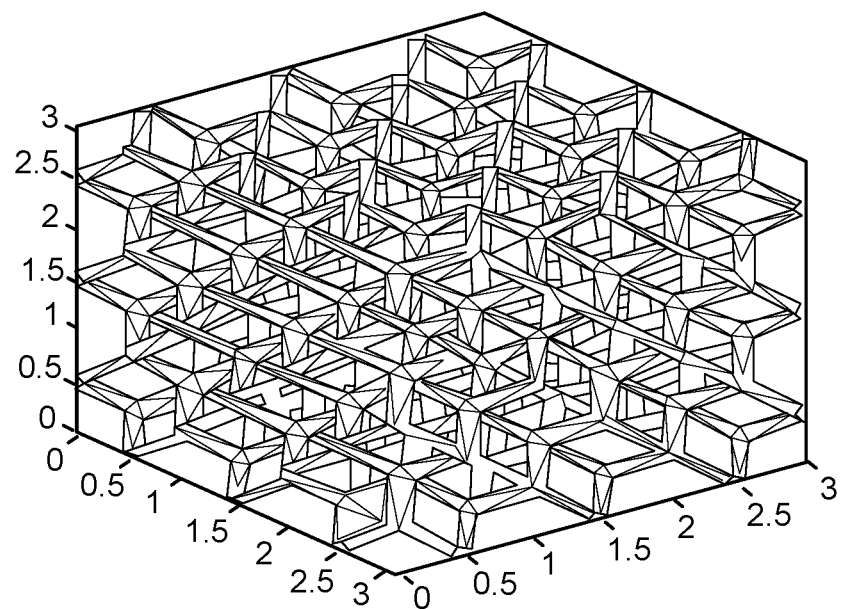
FIG. 5J conceptually depicts a 3-D rendering of the dodecahedron lattice structure, with no node perturbation and no strut size randomization.
Figure 5K:
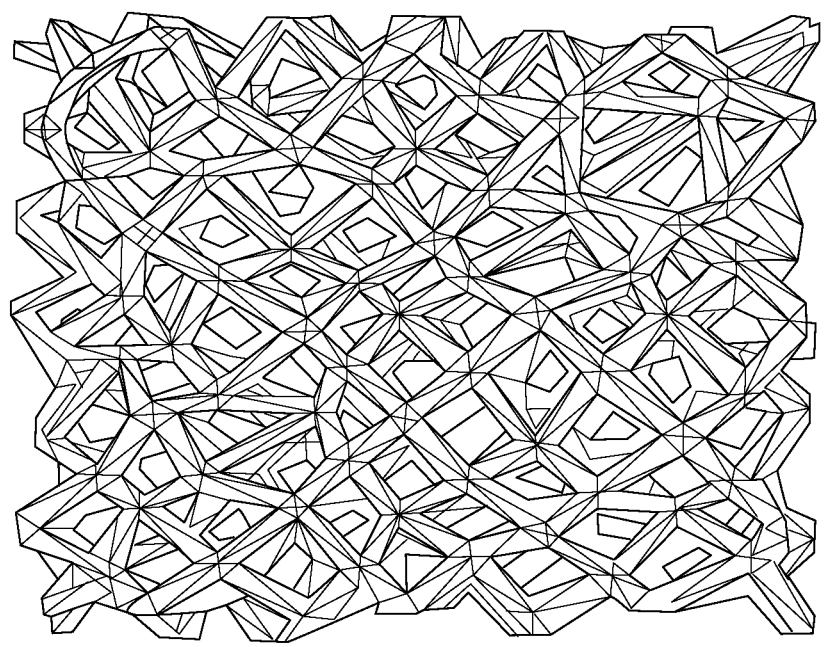
FIG. 5K conceptually depicts a 2-D rendering of a dodecahedron lattice structure, with 20% node perturbation and no strut size randomization.
Figure 5L:
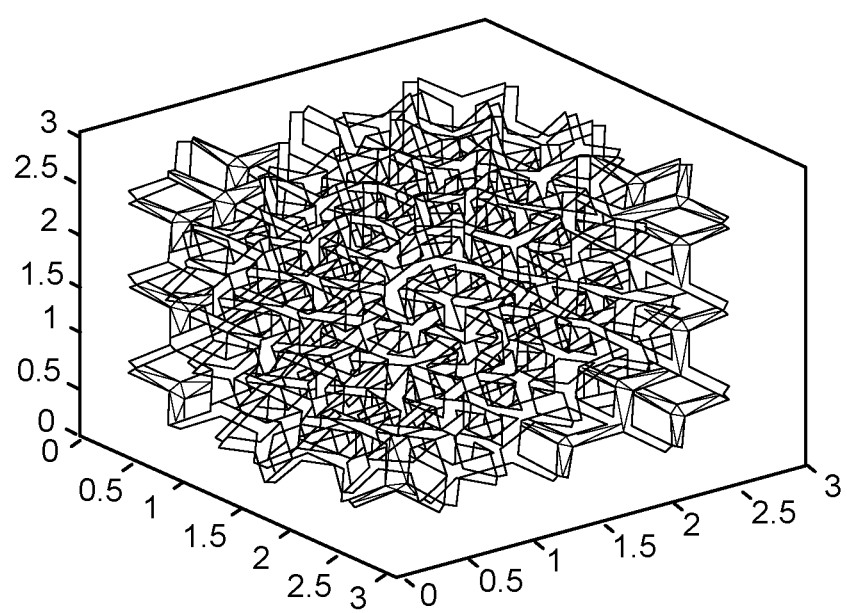
FIG. 5L conceptually depicts a 3-D rendering of the dodecahedron lattice structure, with 20% node perturbation and no strut size randomization.

Referring to FIGS. 2A and 2B, two preferred process flows for fabricating and finishing implants using an abrasive blast are shown. In the first 60, the base metal portion of the implant is formed by machining or additive manufacturing 62,64, prior to the porous layer and needles being additively disposed on the bone-opposition surface of the implant 66. The resulting structure is then finished with an abrasive blast 68. In the second 70, the base metal portion of the implant is again formed by machining or additive manufacturing 72,74, prior to the porous layer and needles being additively disposed on the bone-opposition surface of the implant 76. The resulting structure is then machined into the final implant form 78 and finished with an abrasive blast 80. Alternatively, the resulting structure is then abrasively blasted 82 and finished into the final implant form by machining 84.

FIGS. 3A and 3B and 4A and 4B contrastingly depict SEM images of porous implant sections that have and have not undergone an abrasive blasting step. As can be seen from the images, the non-blasted samples are mostly smooth if viewed on the 20 or 100-µm scale, whereas the blasted samples are almost entirely rough, when viewed at similar magnification. This blast process creates a texture approximately 1-20 µm in scale. This is an ideal scale for micro-texture because it helps osteoblasts adhere to the titanium struts and needles. The blast material is not deposited on the struts and needles (as an HA coating would be). It simply textures the titanium surface by erosion.

In accordance with the invention, the preferred abrasive blast process utilizes an MCD apatitic abrasive (multi-phased calcium phosphate containing HA, TCP and other CaP phases. The blast media has a 125-180-µm size range, for example. The process utilizes a Comco AccuFlo® standard tank micro-abrasive blaster, equipped with Simoom® Technology and a PowderGate® valve. The tank orifice is 0.40 in.; the nozzle is 0.060 in.; the pressure is 90+/−5 psi. A satisfactory roughness has been achieved when the blast does not further affect the visual appearance, specifically the color and reflectivity of the device. Machined devices may require a blast touch up subsequent to machining.

FIGS. 5A-5L illustratively depict the concept of slightly-irregular lattices that are ideally adapted for additive manufacturing in accordance with the present invention. As shown in these figures, node perturbation refers to the location of intersecting struts. In accordance with this aspect of the invention, such intersection locations can be randomized such that the node deviates from a uniform lattice by a randomized distance or degree. Strut size randomization refers to a deviation in cross-sectional dimension (e.g., strut diameter), as well as shape and length. Discrete struts in a lattice could have different cross-sectional sizes, or the struts could have a diameter gradient from one end to the other. These parameters can be randomized for greater diversity in the lattice's geometry. Such slightly-irregular lattices can be used to fabricate any sort of medical implant for which regular lattices might otherwise be used.

Exemplary fusion/fixation devices fabricated by the additive techniques of the present invention may utilize multi-circular cross-sectional profiles (either uniform or tapered), and preferably include exterior needles, preferably oriented in a direction that would resist removal of the implant. Multi-circular cross-sectional profiles, by way of example, have the distinct advantage of not requiring one or more bore broaching steps, thus making insertion quicker and reducing patient infection risk.

It should be understood that the novel structures disclosed and enabled by the present invention are not limited exclusively to those manufactured using additive manufacturing. Indeed, as persons skilled in the art will appreciate, other known surface modification techniques may be used to produce the osteoporous, osteo-derived, and/or needle-containing textures of the inventive implants.

Again, generally speaking, and without intending to be limiting, one aspect of the present invention relates to improved medical implants that include, for example, at least the following: a primary structure formed from metal; and at least one needle-populated, metallic surface portion formed on at least one exterior portion of the primary structure, the at least one surface portion located such that it engages with a patient's bone when the implant is implanted in the patient. Such needle-populated, metallic surface portions may contain, for example, a collection of at least fifty, a hundred, two hundred, five-hundred or more needles, and may be further characterized by at least one, two, three, four, five or more of the following characteristics: (a) the needles in the collection are all oriented substantially normal to the surface portion; (b) the needles in the collection are all oriented in substantially the same direction, with the direction being other than normal to the surface portion; (c) the needles in the collection are all oriented in substantially the same direction, with the direction being other than normal to the surface portion, but within 15 degrees from the normal direction; (d) the needles in the collection are all oriented in substantially the same direction, with the direction being other than normal to the surface portion, and more than 15 degrees from the normal direction; (e) the collection includes needles oriented in at least three different directions relative to the surface portion; (f) the collection includes needles oriented in at least five different directions relative to the surface portion, with all of the needles oriented within 20 degrees from the surface portion normal direction; (g) all of the needles in the collection have substantially the same height; (h) the collection includes needles of at least three different heights; (i) all of the needles in the collection have substantially the same shape; (j) the collection includes needles of at least two different shapes; (k) the needles are distributed substantially uniformly over the surface portion; (l) the needles are distributed non-uniformly over the surface portion; (m) all of the needles in the collection are anchored to the primary structure; (n) most of the needles in the collection are anchored to the primary structure; (o) most of the needles in the collection are anchored to structural elements contained within an osteo-porous, osteo-derived or trabecular coating on the at least one exterior portion of the primary structure; and/or (p) all of the needles in the collection are anchored to structural elements contained within an osteo-porous, osteo-derived or trabecular coating on the at least one exterior portion of the primary structure. The at least one exterior portion preferably includes at least one osteo-porous surface, which may comprise at least one osteo-derived surface. The at least one osteo-porous surface and the needles may be simultaneously formed by an additive manufacturing process, such as, but not limited to, EBM or DMSLS. The primary structure may comprise, for example, an ALIF cage, portions of a bone screw, a dental implant, a foot-and-ankle or long-bone osteotomy wedge, an intervertebral fusion device, a tibial/femoral augment or spacer, a tibial tray portion of a knee implant, a femoral component portion of a knee implant, a primary hip implant, a revision hip implant, a hip trauma component, an acetabular cup, a hip acetabular augment, or other appropriate structure.

Again, generally speaking, and without intending to be limiting, another aspect of the present invention relates to method(s) for making a medical implants with at least one osteo-porous surface by, for example: forming at least a portion of a primary structure of the implant; and forming at least one needle-populated, metallic surface portion on at least one exterior portion of the primary structure using an additive manufacturing technique, the at least one needle-populated surface portion located such that it engages with a patient's bone when the implant is implanted in the patient.

The exemplary flow starts with a spongy bone sample, which is micro CT scanned to obtain 3D scan data, which is then processed into solid model data representing an osteo-porous or osteo-derived texture. This texture data is then combined with data representing the overall implant geometry to create a fabrication file for use by either of the manufacturing steps that follow. The fabrication file may utilize any recognizable solid model specification, such as ".amf" format or ".stl" format, and may be embodied on any sort of permanent storage medium (e.g., CD, CD-ROM, flash), semi-permanent (e.g., SRAM) or transitory (e.g., DRAM) storage medium, or embodied in a coded data signal.

An additional step can be inserted that adds outwardly-protruding "needles" on the outer surface(s) of the osteo-porous and/or osteo-derived coating(s). Such needles substantially increase the coefficient of friction of the coating. Having a high coefficient of friction is clinically advantageous because it provides stronger initial fixation, which is important before bone is able to grow onto/into the porous structure. Such needles can be uniformly or non-uniformly distributed along the porous surface. Likewise, various shapes for the needles are possible, including rectangular, pyramidal, conical, tube-shaped, etc. Also, the needles need not be oriented exactly normal to the exterior surface, but are preferably oriented in a substantially normal (e.g., within +/−15 degrees from normal) orientation. Furthermore, the orientation and/or shape of all needles need not be the same, and the needles may be rendered on selected portions, or the entirety, of the exterior coated surface(s).

Utilizing these or similar techniques, one can efficiently and advantageously form (and/or finish) implants. Finally, it should be understood that the novel structures disclosed and enabled by the present invention are not limited exclusively to those manufactured using additive manufacturing. Indeed, as persons skilled in the art will appreciate, other known surface modification techniques may be used to produce the osteoporous, osteo-derived, and/or needle-containing textures of the inventive implants.

Figure 6A:
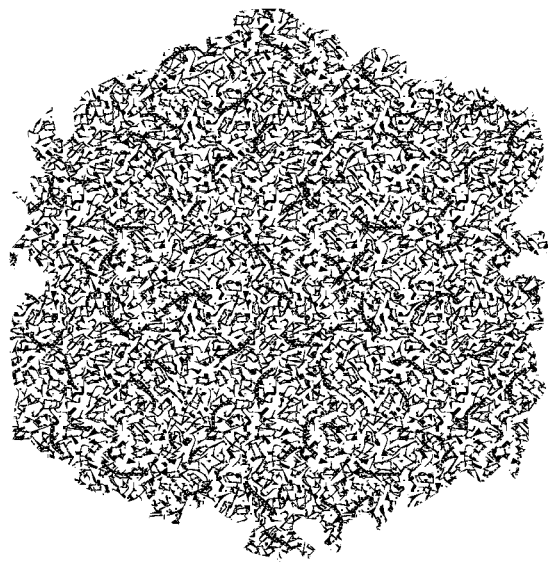
FIG. 6A depicts an illustrative, irregular (e.g., trabecular, osteo-porous, and/or osteo-derived) unit cell appropriate for additive manufacture in accordance with the invention.
Figure 6B:
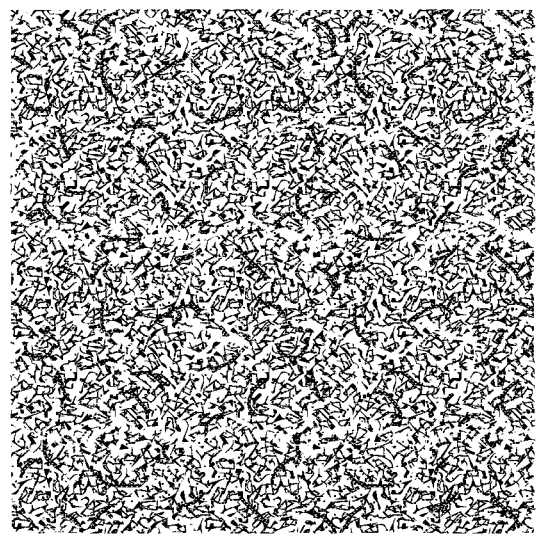
FIG. 6B shows the unit cell of FIG. 6A repeated in a 3×3 array.
Figure 6C:
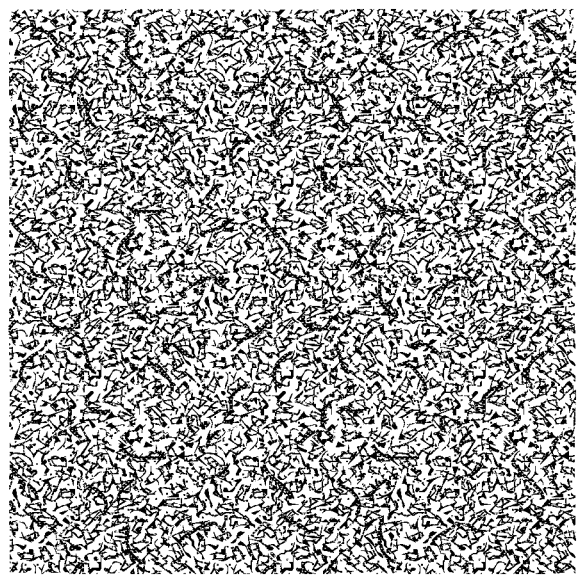
FIG. 6C shows the unit cell of FIG. 6A repeated in a 6×6 array.
Figure 6D:
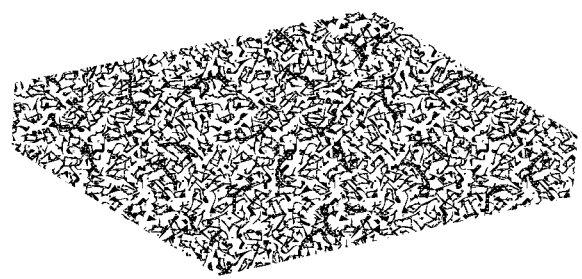
FIG. 6D shows an isometric view of a 9×9 array of the unit cell of FIG. 6A.
Figure 6E:
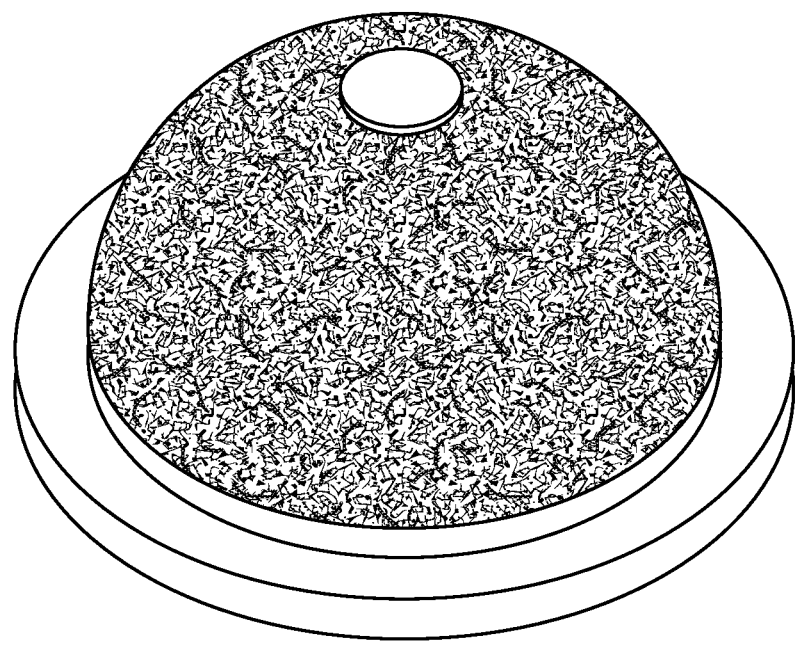
FIG. 6E shows the unit cell of FIG. 6A patterned across the surface of an acetabular shell.
Figure 6F:
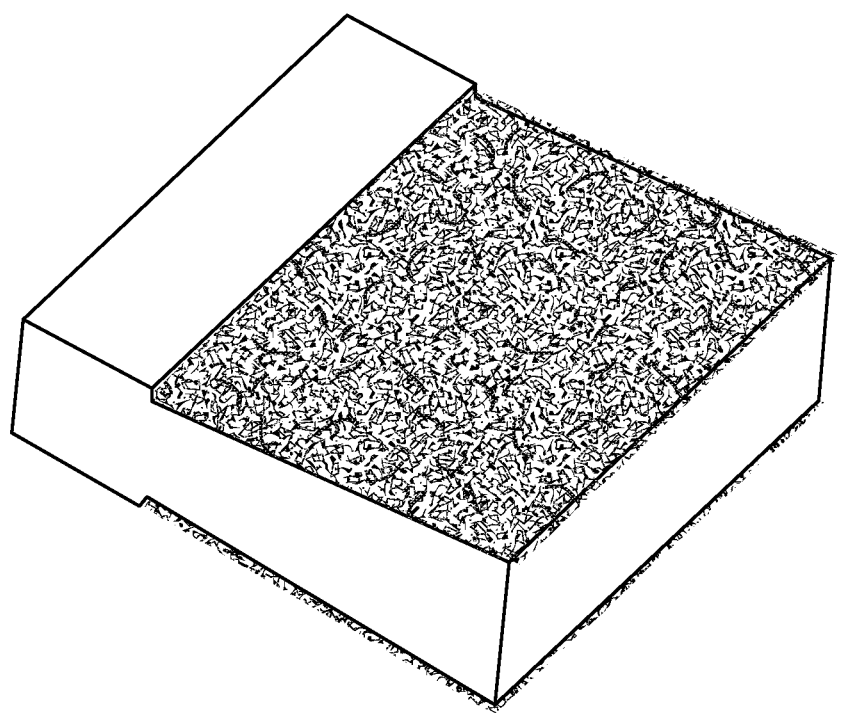
FIG. 6F shows the unit cell of FIG. 6A patterned across the surface of an ALIF cage "blank."

FIG. 6A depicts an illustrative, irregular (e.g., trabecular, osteo-porous, and/or osteo-derived) unit cell appropriate for additive manufacture in accordance with the invention. FIG. 6B shows the unit cell of FIG. 6A repeated in a 3×3 array. FIG. 6C shows the unit cell of FIG. 6A repeated in a 6×6 array. FIG. 6D shows an isometric view of a 9×9 array of the unit cell of FIG. 6A. FIG. 6E shows the unit cell of FIG. 6A patterned across the surface of an acetabular shell. FIG. 6F shows the unit cell of FIG. 6A patterned across the surface of an ALIF cage "blank."

Figure 7:
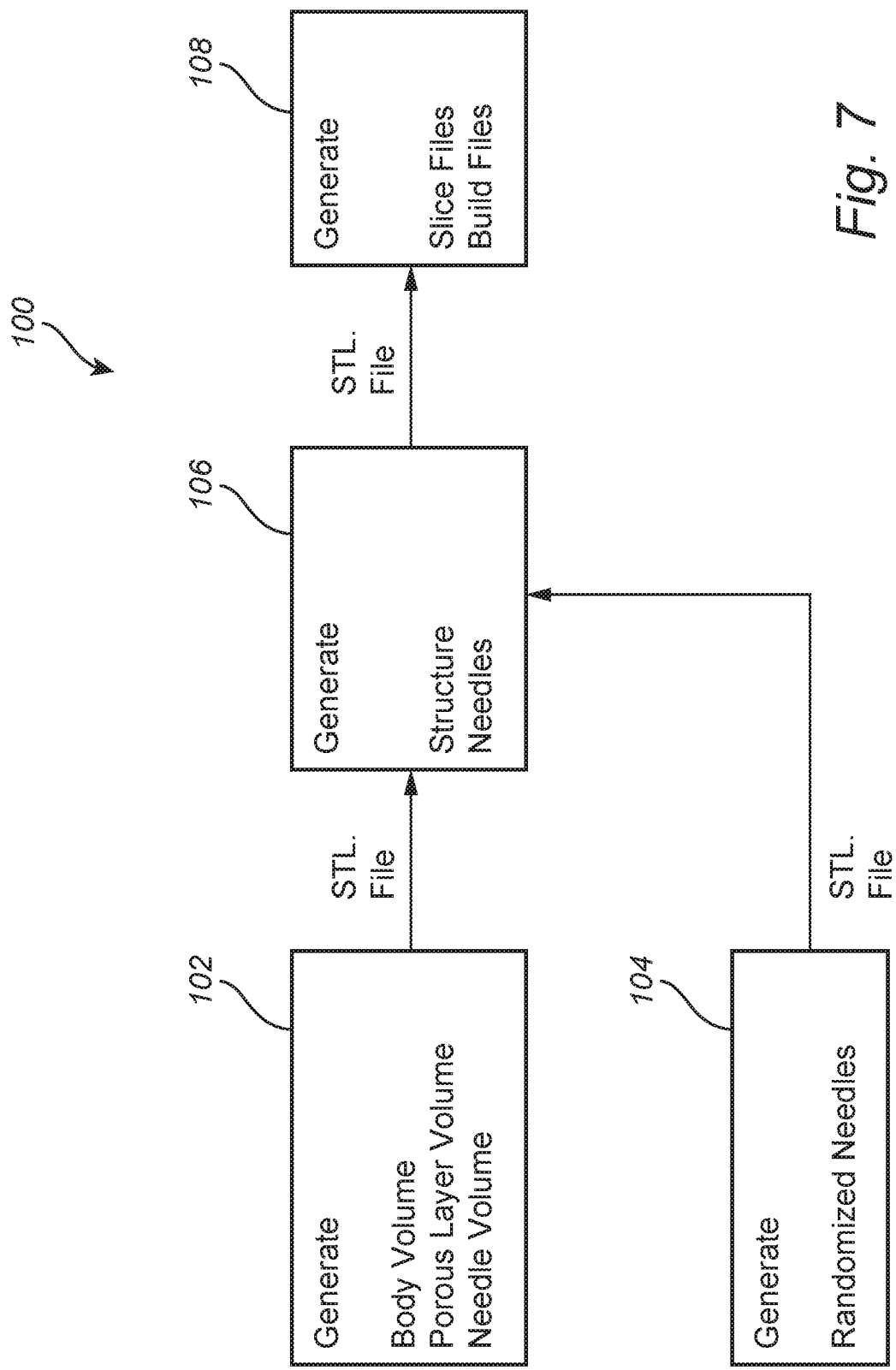
FIG. 7 illustrates one exemplary embodiment of the additive manufacturing modeling and file-generation methodology of the present invention, by which the associated structure(s) are formed.

Referring to FIG. 7, the methodology 100 and implant of the present invention generate and provide a surface that includes the implant body 40 (or "melt") and a porous layer 50 (or "structure") that is disposed directly adjacent to the implant body 40. The porous layer 50 can be additively manufactured on top of the implant body 40, or can be additively manufactured with the implant body 40. The porous layer 50 consists of a bone-interfacing lattice of macroscopic, randomly distributed stochastic struts 52 of various thicknesses, shapes, and intersection points. This lattice is comparable to cancellous bone in terms of pore size and overall porosity, thus it elicits a favorable bone response when applied to the bone-opposition surfaces of the associated implant to which it is applied. The generation of the overall structure is accomplished through several CAD modeling programs in the following data preparation process flow. CAD modeling software is used to generate the design envelope (i.e. the volumes) and spatial relationship (i.e. the overlap) of the various structural elements 102,104. The overall structure is comprised of three specific volume elements: the melt volume, structure volume, and the needle volume. The melt volume is the CAD volume that defines the solid substrate that the structure and needles interface and overlap to ensure a mechanical interface during the additive manufacturing process. For most scenarios, the melt volume is the bulk of the device. The structure volume is the CAD volume that defines the virtual boundary conditions for which the random, stochastic structure will be generated. The structure volume is purely solid and without any lattice. The needle volume is the CAD volume that defines the virtual boundary conditions for which the random, protrusions will extend beyond the regions of the structure volume. The needle volume is purely solid and without any needles (i.e. protrusions). A CAD assembly combines the melt volume, structure volume, and needle volume part models. The structure volume and needle volume elements overlap with the melt volume within the defined coordinate system through the mate interface GUI. This overlap is based on the resolution and accuracy of the intended additive manufacturing technology for which the device will be manufactured. After the CAD assembly has been defined, the models are exported as .STL file format. The .STL files are imported into additional CAD software and used to generate the structure and needles from the structure volume and needle volume elements that were previously defined 106. Using the structure volume, the user executes the GUI algorithm. This algorithm applies a unit cell within a defined volume relative to the CAD environment's coordinate system. The algorithm executes a Boolean operation between the array of unit cells and the structure-volume to yield only the portions of the unit cell within the volume. The overall structure utilizes a porous structure unit cell of defined dimensions, shape, and volume. The algorithm is used to duplicate the porous structure unit cell as an array across the structure volume element and then trim the unit cells within the boundaries of the structure volume. The result is the structure; a random, stochastic lattice that fills the volume of the original structure volume envelope. Similar to structure generation, needles are generated via an intersection Boolean operation between the needle volume element and a pre-programmed. STL file that was generated by an equation-driven algorithm. The pre-programmed needle-element is imported into the CAD software and spatially-aligned with the needle volume. The Boolean is executed and the resulting geometry is an array of randomly located needles (i.e. protrusions) within the boundaries previously defined by the needle volume. After successfully generating the structure and needles, the components are exported as .STL files. The .STL files are then imported into additive manufacturing technology-specific software programs in preparation for the additive manufacturing process. The technology-specific software programs slice the CAD models at a defined thickness acceptable for the additive manufacturing equipment, define the sequence of part build order, and apply exposure strategies. The result of these programs is a build file that is imported and executed on the additive manufacturing machine to yield a physical part.

It is to be recognized that, depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted as one or more instructions or code on a computer-readable medium and executed by a hardware-based processing unit. Computer-readable media may include computer-readable storage media, which corresponds to tangible media, such as data storage media, or communication media, including any medium that facilitates transfer of a computer program from one place to another, e.g., according to a communication protocol. In this manner, computer-readable media generally may correspond to (1) a tangible computer-readable storage medium that is non-transitory or (2) a communication medium, such as a signal or carrier wave. Data storage media may be any available media that can be accessed by one or more computers or one or more processors to retrieve instructions, code, and/or data structures for implementation of the techniques described in this disclosure. A computer program product may include a computer-readable medium.

By way of example, and not limitation, such computer-readable storage media can include random-access memory (RAM), read-only memory (ROM), electrically erasable-programmable read-only memory (EEPROM), compact disc read-only memory (CD-ROM) or other optical disc storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared (IR), radio frequency (RF), and microwave, then the coaxial cable, fiber optic cable, twisted pair, DSL, or wireless technologies, such as IR, RF, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), complex programmable logic devices (CPLDs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims for all purposes.

What is claimed is:

1. A method for manufacturing a surgical implant device, comprising:
   providing a metallic implant body;
   forming a porous layer with an external surface that is microtextured and approximates a scanned three-dimensional spongy bone surface on the metallic implant body, wherein the porous layer comprises an irregular lattice of intersecting struts having randomized strut intersection locations and strut cross-sectional diameters; and
   integrally forming a plurality of needle structures having an external surface that is microtextured with and protruding from the porous layer opposite the metallic implant body by an additive manufacturing process, wherein at least some of the plurality of needle structures are longer and traverse through the porous layer and are coupled directly to the metallic implant body and at least some of the plurality of needle structures are shorter relative to the longer needle structures and are coupled directly only to the porous layer and not to the metallic implant body, and wherein the plurality of needle structures increase the coefficient of friction of an exterior surface of the surgical implant device.

2. The method for manufacturing the surgical implant device of claim 1, wherein the plurality of needle structures that traverse through the porous layer and are coupled directly to the metallic implant body are also coupled to one or more intersecting struts of the lattice.

3. The method for manufacturing the surgical implant device of claim 1, wherein the providing, forming, and integrally forming steps comprise, using a software application:
   defining a melt volume corresponding to a volume occupied by the metallic implant body;
   defining a structure volume corresponding to a volume occupied by the porous layer;
   defining a needle volume corresponding to a volume occupied by the plurality of needle structures;
   formulating a lattice pattern within the structure volume;
   formulating a needle pattern within the needle volume; and
   additively manufacturing at least the porous layer using the lattice pattern and the plurality of needle structures using the needle pattern.

4. The method for manufacturing the surgical implant device of claim 1, wherein the intersecting struts of the lattice have a plurality of thicknesses, lengths, cross-sectional shapes, and intersection points.

5. The method for manufacturing the surgical implant device of claim 1, wherein the plurality of needles are disposed substantially normal to a surface of the metallic implant body.

6. The method for manufacturing the surgical implant device of claim 1, wherein the plurality of needles are disposed randomly across a surface of the metallic implant body.

7. The method for manufacturing the surgical implant device of claim 6, wherein the plurality of needles are disposed across the surface of the metallic implant body with a density of about 0.3 needles/mm$^2$.

8. The method for manufacturing the surgical implant device of claim 1, wherein each of the plurality of needles has a substantially rectangular cross-sectional shape.

9. A method for manufacturing a surgical implant device, comprising:
   using a software application, defining a melt volume corresponding to a volume occupied by a metallic implant body;
   using the software application, defining a structure volume corresponding to a volume occupied by a porous layer;
   using the software application, defining a needle volume corresponding to a volume occupied by a plurality of needle structures;
   using the software application, formulating a lattice pattern within the structure volume;
   using the software application, formulating a needle pattern within the needle volume;
   providing the metallic implant body; and
   additively manufacturing at least the porous layer using the lattice pattern and the plurality of needle structures using the needle pattern;

wherein the porous layer is formed with an external surface that is microtextured and approximates a scanned three-dimensional spongy bone surface on the metallic implant body, wherein the porous layer comprises an irregular lattice of intersecting struts having randomized strut intersection locations and strut cross-sectional diameters; and wherein the plurality of needle structures have an external surface that is microtextured and are integrally formed with and protruding from the porous layer opposite the metallic implant body, wherein at least some of the plurality of needle structures are longer and traverse through the porous layer and are coupled directly to the metallic implant body and at least some of the plurality of needle structures are shorter relative to the longer needle structures and are coupled directly only to the porous layer and not to the metallic implant body, and wherein the plurality of needle structures increase the coefficient of friction of an exterior surface of the surgical implant device.

* * * * *